United States Patent [19]

Holyoke, Jr. et al.

[11] Patent Number: 4,906,288

[45] Date of Patent: Mar. 6, 1990

[54] HERBICIDAL PYRIDYL SULFONAMIDES

[75] Inventors: Caleb W. Holyoke, Jr., Newark; Chi-Ping Tseng, Wilmington, both of Del.; William T. Zimmerman, Landenberg, Pa.

[73] Assignee: E. I. Du Pont De Nemours and Company, Wilmington, Del.

[21] Appl. No.: 116,551

[22] Filed: Nov. 4, 1987

Related U.S. Application Data

[63] Continuation-in-part of Ser. No. 770,257, Aug. 28, 1985, Pat. No. 4,723,991, which is a continuation-in-part of Ser. No. 591,314, Mar. 23, 1984, abandoned, which is a continuation-in-part of Ser. No. 493,079, May 9, 1983, abandoned.

[51] Int. Cl.$^4$ .................. A01N 43/40; C07D 213/57; C07D 213/64

[52] U.S. Cl. ............................. 71/94; 71/90; 71/92; 546/261; 546/264; 546/266; 546/268; 546/275; 546/277; 546/284; 546/289

[58] Field of Search ............... 546/289, 292, 268, 284, 546/275, 277, 261, 264, 266; 71/94, 90, 92

[56] References Cited

U.S. PATENT DOCUMENTS 4,741,760  5/1988  Meyer et al. ........................... 71/92

*Primary Examiner*—Alan L. Rotman

[57] ABSTRACT

Certain N-[(pyridyl or pyrimidyl)aminocarbonyl]arylsulfonamides, such as the compound methyl 2-[[N-(3-cyano-4,6-dimethylpyridin-2-yl)aminocarbonyl]aminosulfonyl]benzoate, possess herbicidal activity.

27 Claims, No Drawings

HERBICIDAL PYRIDYL SULFONAMIDES

RELATED APPLICATION

This application is a continuation-in-part of my copending application U.S. Ser. No. 770,257, filed Aug. 28, 1985 U.S. Pat. No. 4,723,991 which is a continuation-in-part of my copending application U.S. Ser. No. 591,314, filed Mar. 23, 1984 abandoned which is a continuation-in-part of my copending application U.S. Ser. No. 493,079, filed May 9, 1983, abandoned.

BACKGROUND OF THE INVENTION

This invention relates to novel N-[(pyridyl or pyrimidyl)aminocarbonyl]arylsulfonamides, to herbicidal compositions containing them and to methods of using them to control the growth of undesired vegetation.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. These are many products commercially available for these purposes, but the search continues for products which are more effective, less costly and environmentally safe.

A number of different types of N-[(heterocyclic)aminocarbonyl]arylsulfonamides are known as herbicides. Two of the first patents to issue on such compounds are U.S. Pat. Nos. 4,169,719 and 4,127,405, issued on Oct. 2, 1979 and Nov. 28, 1978, respectively. These patents disclose compounds of the general formula

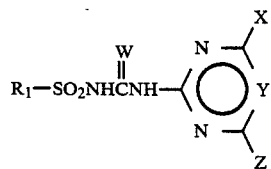

where

R₁ can be optionally substituted benzene, thiophene, pyrrole, furan or unsubstituted naphthalene, and Y is N or CH.

Subsequent patents which have issued have disclosed related compounds with different N-heterocycles. For example, U.S. Pat. No. 4,293,330, issued on Oct. 6, 1981, discloses pyridyl sulfonylureas, and U.S. Pat. No. 4,221,585, issued on Sept. 9, 1980, disclose 4-pyrimidyl sulfonylureas. Nowhere in the art has there been any indication that N-(pyridyl or pyrimidyl)sulfonylurea derivatives, in which the pyridyl or pyrimidyl moiety is substituted ortho- to the sulfonylurea bridge with an electron-withdrawing group, would exhibit high herbicidal activity.

West German patent application No. 3151450A, published 7/14/83, filed by Celamerck discloses sulfamate sulfonylureas of the following general structure.

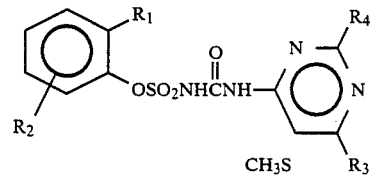

European Publication No. 126,711, published 11/28/84 discloses herbicidal sulfonylureas of the formula

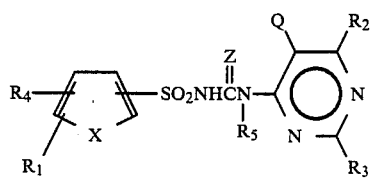

where, in part,

X is O, S, —NR₅—,

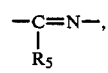

—CH=CH— or an annelated phenyl ring;

Q is, inter alia, halogen, $C_1$-$C_4$ alkyl, nitro, $C_1$-$C_4$ alkoxycarbonyl, $C_1$-$C_4$ alkylsulfonyl;

R₂ and R₃ are independently H, halogen, $C_1$-$C_4$ alkyl, $C_1$-$C_4$ alkoxy, etc.; or Q and R₂ together can also form a 2-4 membered carbon chain, which may still contain an oxygen or sulfur atom, or the group NR₅;

R₁ is H, halogen, nitro or a group

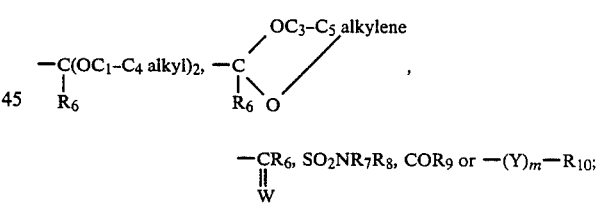

R₄ is H, halogen, $C_1$-$C_4$ alkyl, methoxy, nitro or trifluoromethyl;

Z is O or S;

R₅ is H, $C_1$-$C_4$ alkyl or $C_3$-$C_4$ alkenyl.

SUMMARY OF THE INVENTION

This invention pertains to novel compounds of Formula I, agriculturally suitable compositions containing them, and their method-of-use as preemergent or postemergent herbicides or plant growth regulants.

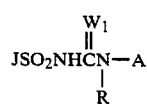

wherein

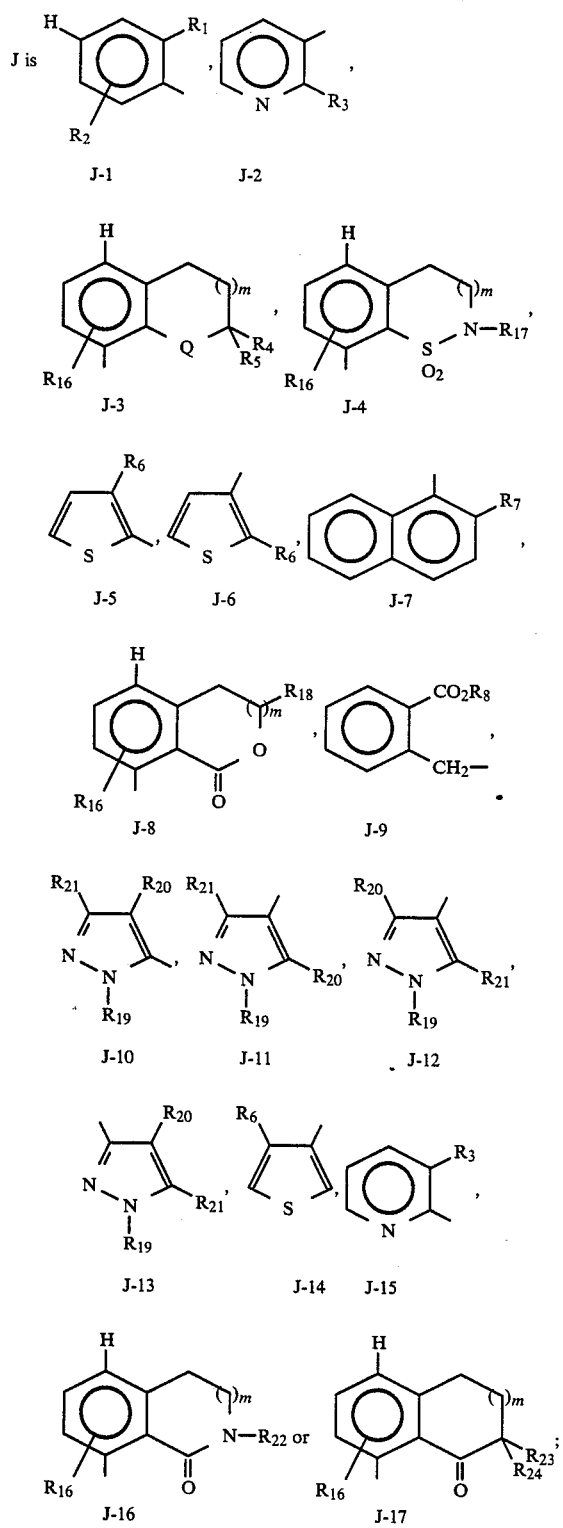
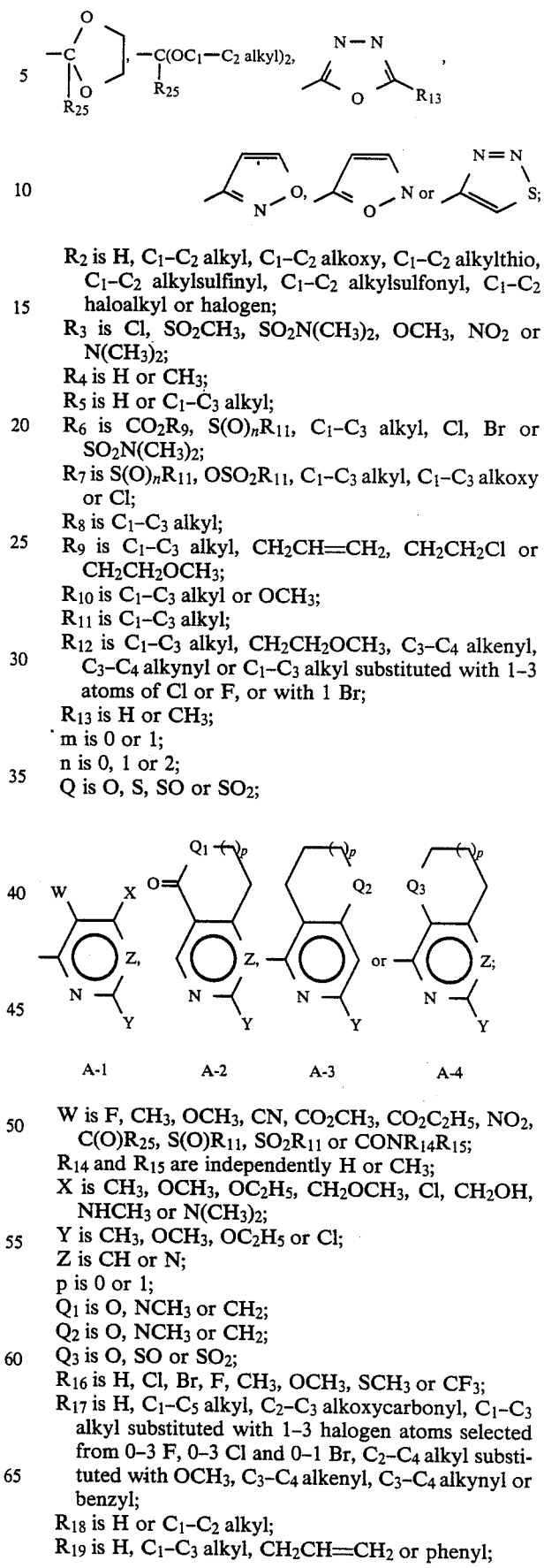

$W_1$ is O or S;

R is H or $CH_3$;

$R_1$ is $NO_2$, Cl, Br, $CF_3$, $C_1$-$C_3$ alkyl, $C_1$-$C_2$ alkyl substituted with $OCH_3$ or $OC_2H_5$, $CO_2R_9$, $SO_2N(CH_3)R_{10}$, $S(O)_nR_{11}$, $S(O)_nCF_2H$, $S(O)_nCF_3$, $OR_{12}$, $OSO_2R_{11}$, $CH_2CH_2Cl$, $C(O)R_{25}$, $R_2$ is H, $C_1$-$C_2$ alkyl, $C_1$-$C_2$ alkoxy, $C_1$-$C_2$ alkylthio, $C_1$-$C_2$ alkylsulfinyl, $C_1$-$C_2$ alkylsulfonyl, $C_1$-$C_2$ haloalkyl or halogen;

$R_3$ is Cl, $SO_2CH_3$, $SO_2N(CH_3)_2$, $OCH_3$, $NO_2$ or $N(CH_3)_2$;

$R_4$ is H or $CH_3$;

$R_5$ is H or $C_1$-$C_3$ alkyl;

$R_6$ is $CO_2R_9$, $S(O)_nR_{11}$, $C_1$-$C_3$ alkyl, Cl, Br or $SO_2N(CH_3)_2$;

$R_7$ is $S(O)_nR_{11}$, $OSO_2R_{11}$, $C_1$-$C_3$ alkyl, $C_1$-$C_3$ alkoxy or Cl;

$R_8$ is $C_1$-$C_3$ alkyl;

$R_9$ is $C_1$-$C_3$ alkyl, $CH_2CH=CH_2$, $CH_2CH_2Cl$ or $CH_2CH_2OCH_3$;

$R_{10}$ is $C_1$-$C_3$ alkyl or $OCH_3$;

$R_{11}$ is $C_1$-$C_3$ alkyl;

$R_{12}$ is $C_1$-$C_3$ alkyl, $CH_2CH_2OCH_3$, $C_3$-$C_4$ alkenyl, $C_3$-$C_4$ alkynyl or $C_1$-$C_3$ alkyl substituted with 1-3 atoms of Cl or F, or with 1 Br;

$R_{13}$ is H or $CH_3$;

m is 0 or 1;

n is 0, 1 or 2;

Q is O, S, SO or $SO_2$;

W is F, $CH_3$, $OCH_3$, CN, $CO_2CH_3$, $CO_2C_2H_5$, $NO_2$, $C(O)R_{25}$, $S(O)R_{11}$, $SO_2R_{11}$ or $CONR_{14}R_{15}$;

$R_{14}$ and $R_{15}$ are independently H or $CH_3$;

X is $CH_3$, $OCH_3$, $OC_2H_5$, $CH_2OCH_3$, Cl, $CH_2OH$, $NHCH_3$ or $N(CH_3)_2$;

Y is $CH_3$, $OCH_3$, $OC_2H_5$ or Cl;

Z is CH or N;

p is 0 or 1;

$Q_1$ is O, $NCH_3$ or $CH_2$;

$Q_2$ is O, $NCH_3$ or $CH_2$;

$Q_3$ is O, SO or $SO_2$;

$R_{16}$ is H, Cl, Br, F, $CH_3$, $OCH_3$, $SCH_3$ or $CF_3$;

$R_{17}$ is H, $C_1$-$C_5$ alkyl, $C_2$-$C_3$ alkoxycarbonyl, $C_1$-$C_3$ alkyl substituted with 1–3 halogen atoms selected from 0–3 F, 0–3 Cl and 0–1 Br, $C_2$-$C_4$ alkyl substituted with $OCH_3$, $C_3$-$C_4$ alkenyl, $C_3$-$C_4$ alkynyl or benzyl;

$R_{18}$ is H or $C_1$-$C_2$ alkyl;

$R_{19}$ is H, $C_1$-$C_3$ alkyl, $CH_2CH=CH_2$ or phenyl;

$R_{20}$ is $C_1$-$C_3$ alkyl, F, Cl, Br, $NO_2$, $CO_2R_9$, $SO_2N(CH_3)R_{10}$, $SO_2R_{11}$, $OCF_2H$ or phenyl;

$R_{21}$ is H, Cl or $CH_3$;

$R_{22}$ is H or $C_1$-$C_3$ alkyl;

$R_{23}$ and $R_{24}$ are independently H or Cl; and $R_{25}$ is H or $C_1$-$C_2$ alkyl;

and their agriculturally suitable salts; provided that (1) X and Y cannot simultaneously be Cl;

(2) when either X or Y is Cl, then Z is CH;

(3) when X and Y are both $CH_3$ and Z is CH, then W is other than $NO_2$;

(4) when Z is N, then $Q_3$ is SO or $SO_2$; and (5) when J is J-11, $R_{19}$ and $R_{20}$ are not both phenyl; and (6) when J is J-1, $R_1$ is $CO_2R_9$, A is A-1 and Z is CH, then W is other than CN.

In the above definitions, the term "alkyl", used either alone or in compound words such as "alkylthio" or "haloalkyl", denotes straight chain or branched alkyl, e.g. methyl, ethyl, n-propyl, isopropyl or the different butyl and pentyl isomers.

Alkoxy denotes methoxy, ethoxy, n-propoxy or isopropoxy.

Alkenyl denotes straight chain or branched alkenes, e.g. 1-propenyl, 2-propenyl, 3-propenyl and the different butenyl isomers.

Alkynyl denotes straight chain or branched alkynes, e.g. ethynyl, 1-propynyl, 2-propynyl and the different butynyl isomers.

The term "halogen", either alone or in compound words such as "haloalkyl", denotes fluorine, chlorine, bromine or iodine. Further, when used in compound words such as "haloalkyl", said alkyl may be monohalogenated or fully substituted with halogen atoms, which may be the same or different. Examples of haloalkyl include $CH_2CH_2F$, $CF_2CF_3$ and $CH_2CHFCl$.

Alkoxycarbonyl denotes methoxycarbonyl or ethoxycarbonyl.

Alkylsulfinyl denotes methylsulfinyl or ethylsulfinyl.

Alkylthio and alkylsulfonyl are defined in an analogous manner.

Preferred for their higher herbicidal activity, greater plant growth regulant activity and/or more favorable ease of synthesis are:

(1) Compounds of Formula I where
  R is H; and
  $W_1$ is O;
(2) Compounds of Preferred 1 where A is A-1;
(3) Compounds of Preferred 1 where A is A-2;
(4) Compounds of Preferred 1 where A is A-3;
(5) Compounds of Preferred 1 where A is A-4;
(6) Compounds of Preferred 1 where J is J-1;
(7) Compounds of Preferred 1 where J is J-2;
(8) Compounds of Preferred 1 where J is J-3;
(9) Compounds of Preferred 1 where J is J-4;
(10) Compounds of Preferred 1 where J is J-5;
(11) Compounds of Preferred 1 where J is J-6;
(12) Compounds of Preferred 1 where J is J-7;
(13) Compounds of Preferred 1 where J is J-8;
(14) Compounds of Preferred 1 where J is J-9;
(15) Compounds of Preferred 1 where J is J-10;
(16) Compounds of Preferred 1 where J is J-11;
(17) Compounds of Preferred 1 where J is J-12;
(18) Compounds of Preferred 1 where J is J-13;
(19) Compounds of Preferred 1 where J is J-14;
(20) Compounds of Preferred 1 where J is J-15;
(21) Compounds of Preferred 1 where J is J-16;
(22) Compounds of Preferred 1 where J is J-17;
(23) Compounds of Preferred 6 where
  $R_1$ is F, Cl, Br, $NO_2$, $CH_3$, $OCH_3$, $OC_2H_5$, $OCH_2CH=CH_2$, $CO_2CH_3$, $CO_2C_2H_5$, $CF_3$, $CH_2CH_2OCH_3$, $SO_2N(CH_3)_2$, $SO_2CH_3$, $SO_2C_2H_5$, $OSO_2CH_3$ or $OSO_2C_2H_5$; and
  $R_2$ is H, F, Cl, $CH_3$, $OCH_3$ or $SCH_3$;
(24) Compounds of Preferred 8 where $R_{16}$ is H;
(25) Compounds of Preferred 9 where $R_{16}$ is H;
(26) Compounds of Preferred 13 where $R_{16}$ is H;
(27) Compounds of Preferred 15 where $R_{21}$ is H;
(28) Compounds of Preferred 16 where $R_{21}$ is H;
(29) Compounds of Preferred 17 where $R_{21}$ is H;
(30) Compounds of Preferred 18 where $R_{21}$ is H;
(31) Compounds of Preferred 21 where $R_{16}$ is H;
(32) Compounds of Preferred 22 where $R_{16}$ is H;
(33) Compounds of Preferred 23 where X and Y are independently $CH_3$ or $OCH_3$; and W is CN, $NO_2$ or $CO_2CH_3$;
(34) Compounds of Preferred 7 where X and Y are independently $CH_3$ or $OCH_3$; and W is CN, $NO_2$ or $CO_2CH_3$;
(35) Compounds of Preferred 24 where X and Y are independently $CH_3$ or $OCH_3$; and W is CN, $NO_2$ or $CO_2CH_3$;
(36) Compounds of Preferred 25 where X and Y are independently $CH_3$ or $OCH_3$; and W is CN, $NO_2$ or $CO_2CH_3$;
(37) Compounds of Preferred 10 where X and Y are independently $CH_3$ or $OCH_3$; and W is CN, $NO_2$ or $CO_2CH_3$;
(38) Compounds of Preferred 11 where X and Y are independently $CH_3$ or $OCH_3$; and W is CN, $NO_2$ or $CO_2CH_3$;
(39) Compounds of Preferred 12 where X and Y are independently $CH_3$ or $OCH_3$; and W is CN, $NO_2$ or $CO_2CH_3$;
(40) Compounds of Preferred 26 where X and Y are independently $CH_3$ or $OCH_3$; and W is CN, $NO_2$ or $CO_2CH_3$;
(41) Compounds of Preferred 14 where X and Y are independently $CH_3$ or $OCH_3$; and W is CN, $NO_2$ or $CO_2CH_3$;
(42) Compounds of Preferred 27 where X and Y are independently $CH_3$ or $OCH_3$; and W is CN, $NO_2$ or $CO_2CH_3$;
(43) Compounds of Preferred 28 where X and Y are independently $CH_3$ or $OCH_3$; and W is CN, $NO_2$ or $CO_2CH_3$;
(44) Compounds of Preferred 29 where X and Y are independently $CH_3$ or $OCH_3$; and W is CN, $NO_2$ or $CO_2CH_3$;
(45) Compounds of Preferred 30 where X and Y are independently $CH_3$ or $OCH_3$; and W is CN, $NO_2$ or $CO_2CH_3$;
(46) Compounds of Preferred 19 where X and Y are independently $CH_3$ or $OCH_3$; and W is CN, $NO_2$ or $CO_2CH_3$;
(47) Compounds of Preferred 20 where X and Y are independently $CH_3$ or $OCH_3$; and W is CN, $NO_2$ or $CO_2CH_3$;
(48) Compounds of Preferred 31 where X and Y are independently $CH_3$ or $OCH_3$; and W is CN, $NO_2$ or $CO_2CH_3$;
(49) Compounds of Preferred 32 where X and Y are independently $CH_3$ or $OCH_3$; and W is CN, $NO_2$ or $CO_2CH_3$;
(50) Compounds of Preferred 33 where A is A-1; and Z is CH;

(51) Compounds of Preferred 34 where A is A-1; and Z is CH;
(52) Compounds of Preferred 35 where A is A-1; and Z is CH;
(53) Compounds of Preferred 36 where A is A-1; and Z is CH;
(54) Compounds of Preferred 37 where A is A-1; and Z is CH;
(55) Compounds of Preferred 38 where A is A-1; and Z is CH;
(56) Compounds of Preferred 39 where A is A-1; and Z is CH;
(57) Compounds of Preferred 40 where A is A-1; and Z is CH;
(58) Compounds of Preferred 41 where A is A-1; and Z is CH;
(59) Compounds of Preferred 42 where A is A-1; and Z is CH;
(60) Compounds of Preferred 43 where A is A-1; and Z is CH;
(61) Compounds of Preferred 44 where A is A-1; and Z is CH;
(62) Compounds of Preferred 45 where A is A-1; and Z is CH;
(63) Compounds of Preferred 46 where A is A-1; and Z is CH;
(64) Compounds of Preferred 47 where A is A-1; and Z is CH;
(65) Compounds of Preferred 48 where A is A-1; and Z is CH;
(66) Compounds of Preferred 49 where A is A-1; and Z is CH;

Specifically preferred for their highest herbicidal activity, greatest plant growth regulant activity and/or most favorable ease of synthesis are:

Methyl 2-[[N-(3-cyano-4,6-dimethylpyridin-2-yl)aminocarbonyl]aminosulfonyl]benzoate, m.p. 158°–162° C.;

N'-[(3-cyano-4,6-dimethylpyridin-2-yl)aminocarbonyl]-N,N-dimethyl-1,2-benzenedisulfonamide, m.p. 163°–165° C.;

Methyl 2-[[N-(2,6-dimethoxy-5-nitropyrimidin-4-yl)aminocarbonyl]aminosulfonyl]benzoate, m.p. 150°–152° C.(d); and Methyl 2-[[(2-dimethylaminosulfonylphenyl)sulfonylamino]carbonylamino]-4,6-dimethylpyridin-3-carboxylate, m.p. 198°–201° C.

DETAILED DESCRIPTION OF THE INVENTION

Synthesis

The compounds of Formula I can be prepared by reacting an appropriate aminoheterocycle of Formula II with an appropriately substituted sulfonyl isocyanate or sulfonyl isothiocyanate of Formula III, as shown in in Equation 1.

Equation 1

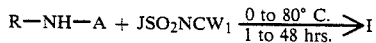

wherein A, J, $W_1$ and R are as previously defined.

The reaction of Equation 1 is best carried out in inert organic solvents such as methylene chloride, tetrahydrofuran, or acetonitrile, at ambient pressure and temperature. The mode of addition is not critical; however, it is often convenient to add the sulfonyl isocyanate to a stirred suspension or solution of the aminoheterocycle. Since such isocyanates usually are liquids, their additions can be easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane or ethyl ether, and filtration.

The sulfonyl isocyanates III used as starting materials are generally known in the art and can be prepared by known methods. One method involves reacting an appropriate benzene or heterocyclic sulfonamide with phosgene in the presence of an alkyl isocyanate, such as n-butyl isocyanate, and a tertiary amine catalyst, such as 1,4-diazabicyclo[2.2.2]octane, at reflux in a solvent such as xylene or chlorobenzene. See H. Ulrich and A. A. Y. Sayigh, *Newer Methods of Preparative Organic Chemistry*, Vol. VI, p. 223–241, Academic Press, New York and London, W. Foerst Ed.

The sulfonyl isocyanates III can also be prepared from sulfonamides by a two step procedure involving (a) reacting the sulfonamides with an alkyl isocyanate in the presence of a base such as $K_2CO_3$ at reflux in an inert solvent such as 2-butanone, forming an alkylsulfonylurea, and (b) reacting this compound with phosgene and tertiary amine catalyst at reflux in xylene solvent.

Sulfonyl isothiocyanates can be prepared according to the methods described by K. Hartke, *Arch. Pharm.*, 299, 174 (1966).

The preparation of sulfonamides from ammonium hydroxide and sulfonyl chlorides is widely reported in the literature, e.g. Crossley et al., *J. Am. Chem. Soc.*, 60, 2223 (1938). Certain sulfonyl chlorides are best prepared by chlorosulfonation of a substituted benzene, naphthalene, or thiophene in carbon tetrachloride according to the teaching of H. T. Clarke et al., *Org. Synth., Coll. Vol.* 1, 2nd Ed. 1941, p. 85. Other sulfonyl chlorides can be made by diazotization of the appropriate amine with sodium nitrite in HCl, followed by reaction of the diazonium salt with sulfur dioxide and cuprous chloride in acetic acid according to the teachings of H. L. Yale and F. Sowinski, *J. Org. Chem.* 25, 1824 (1960).

More specifically, the compounds of this invention may be prepared as described above by the route illustrated below.

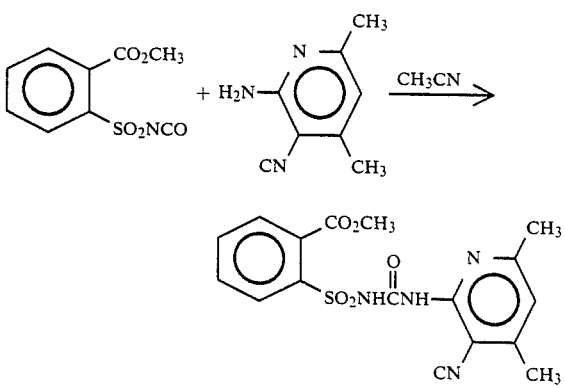

Reference to the following patents is suggested for further details regarding the preparation of the sulfonyl isocyanates III: U.S. Pat. No. 4,169,719, U.S. Pat. No. 4,127,405, U.S. Pat. No. 4,238,621 and EP-A-107,979.

Appropriately substituted aminoheterocycles of Formula II, where R=H and A is a substituted 2-pyridyl or 4-pyrimidyl moiety are generally known in the art and are reviewed in *The Chemistry of Heterocyclic Compounds*, "Pyridine and its Derivatives", Vol. 14, Suppl. Parts I and III (1974), and "The Pyrimidines" (1962) and Suppl. 1 (1970), (John Wiley and Sons, Inc., New York). Commonly used starting materials for the synthesis of such substituted heterocycles are malononitrile, cyanoacetates, cyanoacetamides, ethoxy methylene malononitriles, ammonia, urea, β-diketones, β-ketoesters, malonates, alkylamidines and alkylsulfonylacetonitriles. Some literature techniques are illustrated below. Using these techniques or suitable modifications that would be apparent to one skilled in the art, the 2-aminopyridine and 4-aminopyrimidine intermediates can be readily prepared.

Condensation of ethoxyethylidenemalononitrile and acetamidine yields the corresponding 4-aminopyrimidine-5-carbonitrile as reported, *Chem. Ber.*, 71, 87 (1938).

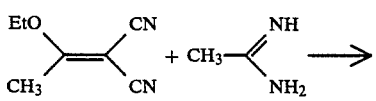

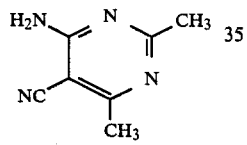

The following sequence of reactions is reported [*J. Med. Chem.*, 24, 382 (1981)] to yield chloro and alkoxy substituted 4-aminopyrimidine-5-carbonitriles.

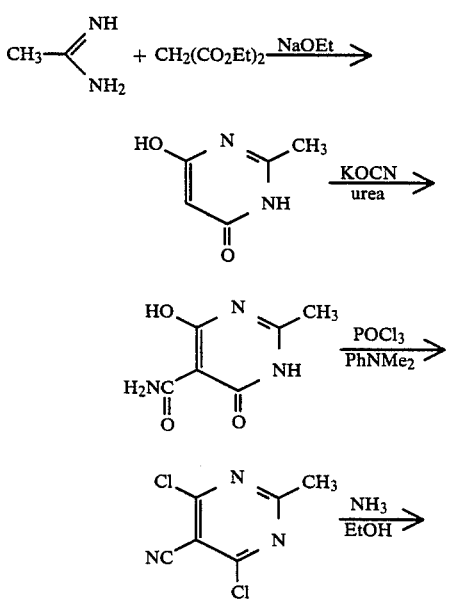

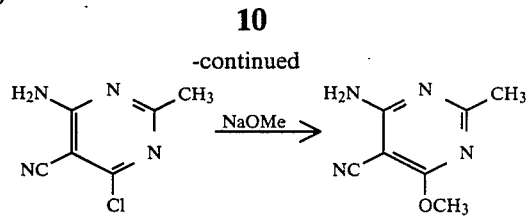

Treatment of methyl cyanoacetate with ethanolic hydrogen chloride affords the imidate which is condensed with acetylacetone as described [*Chem. Ber.*, 73, 542 (1940)] to give the 2-aminopyridine-3-carboxylate.

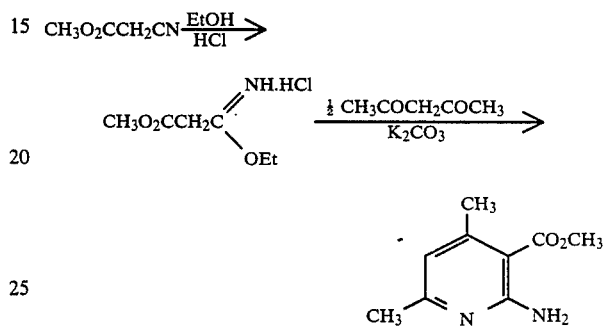

Heterocyclic amines II in which W is a nitro group are prepared by nitration of the corresponding unsubstituted amine as is reported for 2-amino-4,5-dimethyl-3-nitropyridine, *Rocz. Chem.*, 37, 385 (1963), [*Chem. Abstr.*, 59, 11486 (1963)].

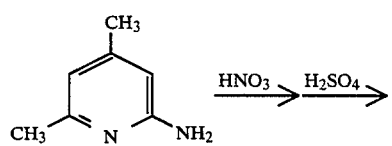

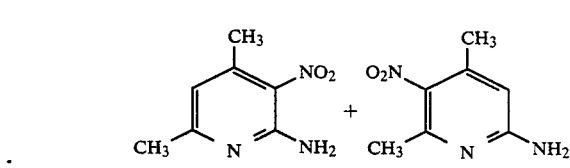

Those intermediates of Formula II in which A is A-2, A-3 or A-4 may be readily prepared by known methods or modifications of these methods. Reference to the following publications is suggested for further details: Brit. Patent GB 1,057,612, U.S. Pat. No. 3,318,881, Belg. Patent BE 895995A, Japan. Kokai JP 48/72197, Japan Kokai JP 48/72169, U.S. Pat. No. 4,209,620, T. R. Kasturi et al., *Tet. Lett.*, 21(9) 865-6, and Y. D. Smirnov et al., *Zh. Prikl. Khim.*, 44(12), 2758-9.

Those intermediates of Formula II in which R is a methyl group may be readily prepared from the corresponding aminoheterocycles (R=H) by known methods for the monomethylation of heterocyclic amines; *J. Chem. Soc. Perkin I*, 1569 (1981).

Agriculturally suitable salts of the compounds of Formula I are also useful herbicides and can be prepared in a number of ways known to the art. Suitable salts include alkali or alkaline earth metal salts, e.g. calcium, potassium or sodium salts; quaternary amine salts; and acid addition salts, e.g., p-toluenesulfonic acid or trichloroacetic acid addition salts.

The following examples teach the preparation of compounds of this invention in more detail. Unless otherwise indicated, all parts are by weight and temperatures in °C.

EXAMPLE 1

N-[(3-Cyano-4,6-dimethylpyridin-2-yl)aminocarbonyl]-2-nitrobenzenesulfonamide (I; J=J-1, $R_1$=$NO_2$, $R_2$=H; Z=CH, W=CN, X=Y=$CH_3$, R=H)

To a stirred suspension of 0.5 g (3.4 mmol) 2-amino-4,6-dimethyl-3-pyridinecarbonitrile [*Archiv. Pharm.*, 288, 174 (1955)] in 20 ml of acetonitrile was added 1.3 g (5.7 mmol) o-nitrobenzenesulfonyl isocyanate. The mixture was then heated to reflux (80°) for four hours followed by stirring at ambient temperature overnight. A crystalline product was collected, 0.5 g, m.p. 174°-176° dec. An infrared spectrum (nujol mull) exhibited absorptions at 1700, 1720 and 2240 cm$^{-1}$; and a proton magnetic resonance spectrum (90 MHz NMR) exhibited absorptions at 2.5 (s, 3H), 2.6 (s, 3H), 7.05 (s, 1H), 7.7 (s br, NH), 7.8 (m, 3H), 8.4 (m, 1H), 9.7 (s br, NH) ppm indicating the title compound.

EXAMPLE 2

2-Chloro-N-[(4,6-dimethyl-3-methoxycarbonylpyridin-2yl)aminocarbonyl]benzenesulfonamide (I; J=J-1, $R_1$=Cl, $R_2$=H; Z=CH, W=$CO_2CH_3$, X=Y=$CH_3$, R=H)

A mixture of 0.5 g (2.8 mmol) methyl 2-amino-4,6-dimethylpyridine-3-carboxylate [preparation analogous to ethyl ester: *Chem. Ber.*, 73, 542 (1940)] and 0.78 g (3.6 mmol) o-chlorobenzenesulfonyl isocyanate were combined in 40 ml acetonitrile and stirred at ambient temperature for forty-eight hours. The homogeneous mixture was then evaporated and triturated with n-chlorobutane to afford 1.04 g of product, m.p. 175°-177°. IR (nujol) 1670, 1710 cm$^{-1}$; and NMR ($CDCl_3$) 2.58 (s, 3H), 2.60 (s, 3H), 3.95 (s, 3H), 6.85 (s, 1H), 7.55 (m, 3H), 8.40 (m, 1H), 10.2 (s br, NH), 14.2 (s br, NH) ppm indicated the title compound.

EXAMPLE 3

2,6-Dimethoxy-5-nitro-4-pyrimidinamine (II; Z=N, W=$NO_2$, X=Y=$OCH_3$)

To a solution of 20 ml of concentrated nitric acid and 16 ml of concentrated sulfuric acid was added 3.9 g (0.025 mmol) of 2,6-dimethoxy-4-pyrimidinamine. The resulting solution was stirred at ambient temperature and pressure for thirty minutes and was then stirred at 50° for fifteen minutes. The solution was then cooled in an ice bath to ~0° C. The solid was collected by filtration, washed with water and dried in an oven at 60° C. to afford 3.6 g of the title compound, m.p. 178°-179° C.

NMR (DMSO-$d_6$)δ: 3.96 (d, 6H); and 8.2 (broad s, 2H) ppm.

EXAMPLE 4

2-[[(2,6-Dimethoxy-5-nitropyrimidin-4-yl)aminocarbonyl]aminosulfonyl]benzoic acid, methyl ester (I; J=J-1, $R_1$=$CO_2CH_3$, $R_2$=H; Z=N, W=$NO_2$, X=Y=$OCH_3$, R=H)

A solution of 0.2 g (1.0 mmol) of 2,6-dimethoxy-5-nitro-4-pyrimidinamine and 0.6 g (2.4 mmol) of 2-carbomethoxybenzenesulfonyl isocyanate in 15 ml of methylene chloride was stirred at ambient temperature and pressure for 12 hours under anhydrous conditions. The solvent was then evaporated under reduced pressure. The residue was stirred in n-butyl chloride (70 ml). The solid was then collected by filtration, washed with ether and then dried in an oven to afford 0.4 g of the title compound, m.p. 150°-152° dec.

NMR (DMSO-$d_6$)δ: 3.9-4.1 (m, 9H, $OCH_3$); 7.7-8.5 (m, 4H, ArH); and 10-12 (br, 2H, NH) ppm.

EXAMPLE 5

2-Chloro-N-[(5-cyano-2,6-dimethylpyrimidin-4-yl)-aminocarbonyl]benzenesulfonamide (I; J=J-1, $R_1$=Cl, $R_2$=H; Z=N, W=CN, X=Y=$CH_3$, R=H)

4.35 g of 2-Chlorobenzenesulfonyl isocyanate was dissolved in 10 ml xylenes and 25 ml methylene chloride. To this was added 2.96 g of 4-amino-2,6-dimethyl-5-pyrimidine carbonitrile and a catalytic amount of 1,4-diazabicyclo[2.2.2]octane. The reaction was stirred under a $CaSO_4$ drying tube for three days. The reaction was filtered to remove unreacted pyrimidine, and then the desired product was precipitated by addition of 1-chlorobutane, filtered off, rinsed well with 1-chlorobutane and dried in vacuo giving 5.2 g of the desired product, m.p. 125°-127°. IR: 2240 cm$^{-1}$ (C≡), 1730 cm$^{-1}$ (C=O); NMR (DMSO-$d_6$)δ: 2.6 (s, 6H), 7.4-8.1 (m, 4H) ppm indicating the title compound.

By using techniques analogous to those described in Examples 1 through 5 and/or the processes described above, the compounds of Tables I through II may be prepared.

TABLE I

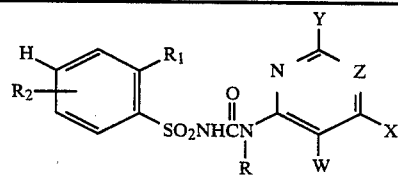

| $R_1$ | $R_2$ | R | W | X | Y | Z | m.p. (°C.) |
|---|---|---|---|---|---|---|---|
| $NO_2$ | H | H | CN | $CH_3$ | $CH_3$ | CH | 174–176(d) |
| $NO_2$ | H | H | CN | $CH_3$ | $CH_3$ | N | 154(d) |
| $NO_2$ | H | H | $CO_2CH_3$ | $CH_3$ | $CH_3$ | CH | |
| $NO_2$ | 6-Cl | H | $CO_2CH_3$ | $OCH_3$ | $CH_3$ | N | |
| F | H | H | $SO_2CH_3$ | $CH_3$ | $CH_3$ | CH | |
| F | H | H | $CO_2CH(CH_3)_2$ | $OCH_3$ | $CH_3$ | CH | |
| F | H | H | $S(O)CH_3$ | $CH_3$ | $CH_3$ | N | |
| Cl | H | H | CN | $CH_3$ | $CH_3$ | N | 125–127 |
| Cl | H | H | CN | $OCH_3$ | $CH_3$ | N | 187–190(d) |
| Cl | H | H | CN | $CH_3$ | $CH_3$ | CH | 175–178(d) |
| Cl | H | H | $CO_2CH_3$ | $CH_3$ | $CH_3$ | CH | 175–177(d) |

TABLE I-continued

| R₁ | R₂ | R | W | X | Y | Z | m.p. (°C.) |
|---|---|---|---|---|---|---|---|
| Cl | H | H | NO₂ | OCH₃ | OCH₃ | N | 143–145(d) |
| Cl | 5-Cl | H | SO₂CH₃ | CH₃ | CH₃ | N | |
| CF₃ | H | H | CN | CH₃ | OCH₃ | CH | |
| CF₃ | H | H | CO₂C₂H₅ | CH₃ | CH₃ | N | |
| Br | H | H | CO₂CH₃ | OCH₃ | CH₃ | CH | |
| CH₃ | H | H | C(O)NH₂ | CH₃ | CH₃ | N | |
| CH₃ | 5-Cl | H | CN | CH₃ | CH₃ | CH | |
| n-C₃H₇ | H | H | CN | CH₃ | CH₃ | CH | |
| CH₂OCH₃ | H | H | CN | CH₃ | CH₃ | N | |
| CH₂OCH₃ | H | H | S(O)CH₃ | CH₃ | CH₃ | N | |
| CH₂CH₂OCH₃ | H | H | CO₂CH₃ | OCH₃ | CH₃ | CH | |
| SCF₂H | H | H | SO₂CH₃ | CH₃ | CH₃ | N | |
| SCF₂H | H | H | NO₂ | OCH₃ | CH₃ | CH | |
| SCF₂H | 5-CH₃ | H | CN | OCH₃ | CH₃ | N | |
| Cl | H | H | CO₂C₂H₅ | CH₃ | CH₃ | CH | 150–152 |
| CO₂CH₃ | H | H | CO₂C₂H₅ | CH₃ | CH₃ | CH | 150–153 |
| SO₂N(CH₃)₂ | H | H | CO₂C₂H₅ | CH₃ | CH₃ | CH | 165–167 |
| OSO₂CH₃ | H | H | CN | CH₃ | CH₃ | N | 138(d) |
| OSO₂CH₃ | H | H | CO₂CH₃ | CH₃ | CH₃ | CH | |
| OSO₂C₃H₇—n | H | H | NO₂ | OCH₃ | OCH₃ | N | |
| OCF₂H | H | H | CO₂CH₃ | OCH₃ | OCH₃ | N | |
| OCH₃ | H | H | CO₂CH₃ | CH₃ | CH₃ | CH | |
| OC₂H₅ | H | H | CN | CH₃ | CH₃ | CH | |
| OC₃H₇—n | H | H | CN | OCH₃ | CH₃ | N | |
| OCH₂CH₂OCH₃ | H | H | S(O)CH₃ | CH₃ | CH₃ | CH | |
| C₂H₅ | H | H | CO₂CH₃ | Cl | CH₃ | CH | |
| i-C₃H₇ | H | H | CO₂CH₃ | CH₃ | CH₃ | CH | |
| SCH₃ | H | H | CN | CH₃ | CH₃ | CH | |
| SCH₃ | H | CH₃ | NO₂ | OCH₃ | OCH₃ | CH | |
| SC₂H₅ | H | H | CO₂CH₃ | CH₃ | CH₃ | N | |
| SC₃H₇—n | H | H | NO₂ | OCH₃ | CH₃ | CH | |
| SO₂CH₃ | H | H | CN | CH₃ | CH₃ | N | 196–201 |
| SO₂CH₃ | H | H | CN | CH₃ | CH₃ | CH | 230–234(d) |
| SO₂CH₃ | H | H | CO₂CH₃ | CH₃ | CH₃ | CH | 187–189 |
| SO₂CH₃ | H | H | NO₂ | OCH₃ | OCH₃ | N | 184–185(d) |
| SO₂CH₃ | H | H | S(O)CH₃ | CH₃ | CH₃ | CH | |
| SO₂C₃H₇—n | H | H | CO₂CH₃ | CH₃ | CH₃ | CH | |
| SO₂C₂H₅ | H | H | NO₂ | CH₃ | OCH₃ | N | |
| SO₂C₃H₇—n | H | H | CN | OCH₃ | OCH₃ | CH | |
| CO₂CH₃ | H | H | CN | CH₃ | CH₃ | N | 167–168 |
| CO₂CH₃ | H | H | CN | CH₃ | CH₃ | CH | 158–162 |
| CO₂CH₃ | H | H | CN | OCH₃ | CH₃ | N | 170–172 |
| CO₂CH₃ | H | H | CO₂CH₃ | CH₃ | CH₃ | CH | 159–161 |
| CO₂CH₃ | H | H | NO₂ | OCH₃ | OCH₃ | N | 150–152 |
| CO₂CH₃ | H | H | CN | Cl | CH₃ | CH | |
| CO₂CH₃ | 3-CH₃ | H | S(O)CH₃ | CH₃ | CH₃ | CH | |
| CO₂CH₃ | 5-Cl | H | CN | CH₃ | CH₃ | N | |
| CO₂CH₃ | 5-OCH₃ | H | CN | OCH₃ | CH₃ | N | |
| CO₂CH₃ | 5-F | H | SO₂CH₃ | CH₃ | Cl | CH | |
| CO₂CH₃ | 5-CF₃ | H | S(O)C₂H₅ | CH₃ | CH₃ | CH | |
| CO₂CH₃ | H | H | CONHCH₃ | OCH₃ | CH₃ | CH | |
| CO₂CH₃ | H | H | CON(CH₃)₂ | CH₃ | CH₃ | N | |
| CO₂CH₃ | H | H | CON(CH₃)₂ | Cl | CH₃ | CH | |
| CO₂CH₃ | H | CH₃ | CO₂CH₃ | OC₂H₅ | CH₃ | CH | |
| CO₂CH₃ | H | H | CO₂CH₃ | Cl | CH₃ | CH | |
| CO₂CH₃ | H | H | CN | CH₂OCH₃ | CH₃ | N | |
| CO₂CH₃ | 5-Br | H | CN | CH₂OCH₃ | OCH₃ | CH | |
| CO₂CH₃ | H | H | NO₂ | CH₂OCH₃ | CH₃ | N | |
| CO₂CH₃ | H | H | NO₂ | OC₂H₅ | OC₂H₅ | N | |
| CO₂CH₃ | H | H | SO₂CH₃ | Cl | OCH₃ | CH | |
| CO₂CH₃ | H | H | SO₂C₂H₅ | OCH₃ | Cl | CH | |
| CO₂C₂H₅ | H | CH₃ | CN | CH₃ | CH₃ | CH | |
| CO₂C₃H₇—n | H | H | CN | CH₃ | CH₃ | CH | 148–150 |
| CO₂C₂H₅ | H | H | SO₂CH₃ | CH₃ | CH₃ | N | |
| CO₂CH₂CH=CH₂ | H | H | CN | CH₃ | CH₃ | CH | 134–137 |
| CO₂CH₂CH₂Cl | H | H | NO₂ | OCH₃ | OCH₃ | N | |
| CO₂CH₂CH₂OCH₃ | H | H | CO₂CH₃ | CH₃ | CH₃ | CH | |

TABLE I-continued

[Structure: phenyl ring with H at position 4, R₁ ortho, R₂ meta-substituted, bearing -SO₂NHC(O)N(R)- linked to a pyrimidine/triazine ring with substituents W, X, Y, Z]

| R₁ | R₂ | R | W | X | Y | Z | m.p. (°C.) |
|---|---|---|---|---|---|---|---|
| (1,3,4-oxadiazole, 2-methyl, 5-H) | H | H | CN | CH₃ | CH₃ | CH | |
| (1,3,4-oxadiazole, 2-methyl, 5-CH₃) | H | H | CN | CH₃ | CH₃ | N | |
| (isoxazole, 3-methyl) | H | H | CO₂CH₃ | CH₃ | CH₃ | CH | |
| (isoxazole, 5-methyl) | H | H | SO₂CH₃ | CH₃ | CH₃ | N | |
| (1,3,4-thiadiazole, methyl) | H | H | NO₂ | OCH₃ | OCH₃ | N | |
| CO₂CH₃ | 5-Cl | H | CN | CH₃ | CH₃ | CH | 192–195(d) |
| SO₂N(CH₃)₂ | H | H | CN | CH₃ | CH₃ | N | 82 |
| SO₂N(CH₃)₂ | H | H | CN | CH₃ | CH₃ | CH | 163–165 |
| SO₂N(CH₃)₂ | H | H | CN | OCH₃ | CH₃ | N | 193–195 |
| SO₂N(CH₃)₂ | H | H | CO₂CH₃ | CH₃ | CH₃ | CH | 198–201 |
| SO₂N(CH₃)₂ | H | H | NO₂ | OCH₃ | OCH₃ | N | 130–131(d) |
| SO₂N(CH₃)₂ | H | H | S(O)CH₃ | CH₃ | CH₃ | CH | |
| SO₂N(CH₃)₂ | H | H | SO₂CH₃ | CH₃ | CH₃ | N | |
| SO₂N(CH₃)C₂H₅ | H | H | CN | CH₃ | CH₃ | N | |
| SO₂N(CH₃)₂ | H | CH₃ | CN | CH₃ | CH₃ | CH | |
| SO₂NCH(CH₃)₂ CH₃ | 5-Cl | H | CN | CH₃ | CH₃ | CH | |
| SO₂N(CH₃)OCH₃ | H | H | CO₂CH₃ | CH₃ | CH₃ | CH | |
| CH₂OCH₂CH₃ | H | H | CO₂CH₃ | CH₃ | CH₃ | CH | |
| CH₂OCH₂CH₃ | H | H | CN | CH₃ | CH₃ | CH | |
| CH(CH₃)OCH₃ | H | H | CN | CH₃ | CH₃ | CH | |
| CH₂CH₂OC₂H₅ | H | H | NO₂ | OCH₃ | OCH₃ | N | |
| CH(CH₃)OC₂H₅ | H | H | S(O)CH₃ | CH₃ | CH₃ | CH | |
| OCH₂CH=CH₂ | H | H | CN | CH₃ | CH₃ | CH | |
| OCH₂C≡CH | H | H | CO₂CH₃ | CH₃ | CH₃ | CH | |
| OCH₂CH=CHCH₃ | H | H | NO₂ | OCH₃ | OCH₃ | N | |
| OCH₂C≡C—CH₃ | H | H | CN | CH₃ | CH₃ | CH | |
| Cl | H | H | SO₂CH₃ | OCH₃ | OCH₃ | N | 170–173(d) |
| CO₂CH₃ | H | H | SO₂CH₃ | OCH₃ | OCH₃ | N | 180–182(d) |
| SO₂N(CH₃)₂ | H | H | SO₂CH₃ | OCH₃ | OCH₃ | N | 188–190(d) |
| Cl | H | H | S(O)CH₃ | OCH₃ | OCH₃ | N | 191–193(d) |
| CO₂CH₃ | H | H | S(O)CH₃ | OCH₃ | OCH₃ | N | 185–188(d) |
| SO₂N(CH₃)₂ | H | H | S(O)CH₃ | OCH₃ | OCH₃ | N | 193–196(d) |
| NO₂ | H | H | F | CH₃ | CH₃ | CH | |
| NO₂ | H | H | F | CH₃ | CH₃ | N | |
| NO₂ | H | H | OCH₃ | CH₃ | CH₃ | CH | |
| NO₂ | 6-Cl | H | OCH₃ | OCH₃ | CH₃ | N | |
| F | H | H | CHO | CH₃ | CH₃ | CH | |
| F | H | H | C(O)C₂H₅ | CH₃ | CH₃ | N | |
| Cl | H | H | F | CH₃ | CH₃ | N | |
| Cl | H | H | F | OCH₃ | CH₃ | N | |
| Cl | H | H | F | CH₃ | CH₃ | CH | |
| Cl | H | H | OCH₃ | CH₃ | CH₃ | CH | |
| Cl | H | H | CH₃ | OCH₃ | CH₃ | N | |
| Cl | 5-Cl | H | CHO | CH₃ | CH₃ | N | |
| CF₃ | H | H | F | CH₃ | OCH₃ | CH | |
| CF₃ | H | H | OCH₃ | CH₃ | CH₃ | N | |
| Br | H | H | OCH₃ | OCH₃ | CH₃ | CH | |

TABLE I-continued

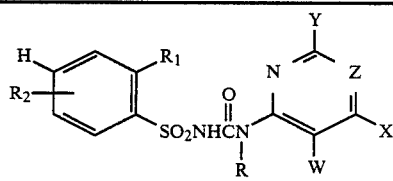

| R₁ | R₂ | R | W | X | Y | Z | m.p. (°C.) |
|---|---|---|---|---|---|---|---|
| CH₃ | H | H | C(O)CH₃ | CH₃ | CH₃ | N | |
| CH₃ | 5-Cl | H | F | CH₃ | CH₃ | CH | |
| n-C₃H₇ | H | H | F | CH₃ | CH₃ | CH | |
| CH₂OCH₃ | H | H | F | CH₃ | CH₃ | N | |
| CH₂OCH₃ | H | H | COC₂H₅ | CH₃ | CH₃ | N | |
| CH₂CH₂OCH₃ | H | H | OCH₃ | OCH₃ | CH₃ | CH | |
| SCF₂H | H | H | CHO | CH₃ | CH₃ | N | |
| SCF₂H | H | H | CH₃ | OCH₃ | CH₃ | CH | |
| SCF₂H | 5-CH₃ | H | F | OCH₃ | CH₃ | N | |
| Cl | H | H | CH₃ | CH₃ | CH₃ | CH | |
| —CHO | H | H | CN | CH₃ | CH₃ | CH | |
| —C(O)CH₃ | H | H | CN | CH₃ | CH₃ | N | |
| —C(O)C₂H₅ | H | H | CO₂CH₃ | CH₃ | CH₃ | CH | |
| —CH(OCH₃)₂ | 6-Cl | H | CO₂CH₃ | OCH₃ | CH₃ | N | |
| CH(OC₂H₅)₂ | H | H | SO₂CH₃ | CH₃ | CH₃ | CH | |
| 1,3-dioxo-lan-2-yl | H | H | CO₂CH(CH₃)₂ | OCH₃ | CH₃ | CH | |
| C(CH₃)(OCH₃)₂ | H | H | S(O)CH₃ | CH₃ | CH₃ | N | |
| C(CH₃)(OC₂H₅)₂ | H | H | CN | CH₃ | CH₃ | N | |
| 1,3-dioxolan-2-methyl-2-yl | H | H | CN | OCH₃ | CH₃ | N | |
| C(C₂H₅)(OCH₃)₂ | H | H | CN | CH₃ | CH₃ | CH | |
| C(C₂H₅)(OC₂H₅)₂ | H | H | CO₂CH₃ | CH₃ | CH₃ | CH | |
| 1,3-dioxolan-2-ethyl-2-yl | H | H | NO₂ | OCH₃ | OCH₃ | N | |
| Cl | OC₂H₅ | H | SO₂CH₃ | CH₃ | CH₃ | N | |
| S(O)CF₃ | H | H | CN | CH₃ | OCH₃ | CH | |
| S(O)₂CF₃ | H | H | CO₂C₂H₅ | CH₃ | CH₃ | N | |
| SCF₃ | H | H | CO₂CH₃ | OCH₃ | CH₃ | CH | |
| CH₃ | C₂H₅ | H | C(O)NH₂ | CH₃ | CH₃ | N | |
| CH₃ | SCH₃ | H | CN | CH₃ | CH₃ | CH | |
| n-C₃H₇ | S(O)CH₃ | H | CN | CH₃ | CH₃ | CH | |
| CH₂OCH₃ | S(O)₂CH₃ | H | CN | CH₃ | CH₃ | N | |
| CH₂OCH₃ | CH₂Cl | H | S(O)CH₃ | CH₃ | CH₃ | N | |
| CH₂CH₂OCH₃ | CH₂CH₂Cl | H | CO₂CH₃ | OCH₃ | CH₃ | CH | |
| S(O)₂CF₂H | H | H | SO₂CH₃ | CH₃ | CH₃ | N | |
| S(O)CF₂H | H | H | NO₂ | OCH₃ | CH₃ | CH | |
| S(O)CF₂H | 5-CH₃ | H | CN | OCH₃ | CH₃ | N | |
| Cl | SC₂H₅ | H | CO₂C₂H₅ | CH₃ | CH₃ | CH | |

TABLE I-a

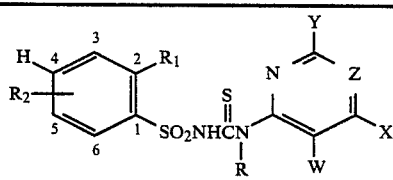

| R₁ | R₂ | R | W | X | Y | Z | m.p. (°C.) |
|---|---|---|---|---|---|---|---|
| NO₂ | H | H | CN | CH₃ | CH₃ | CH | |
| NO₂ | H | H | CN | CH₃ | CH₃ | N | |
| NO₂ | H | H | CO₂CH₃ | CH₃ | CH₃ | CH | |
| NO₂ | 6-Cl | H | CO₂CH₃ | OCH₃ | CH₃ | N | |
| F | H | H | SO₂CH₃ | CH₃ | CH₃ | CH | |
| F | H | H | CO₂CH(CH₃)₂ | OCH₃ | CH₃ | CH | |
| F | H | H | S(O)CH₃ | CH₃ | CH₃ | N | |
| Cl | H | H | CN | CH₃ | CH₃ | N | |
| Cl | H | H | CN | OCH₃ | CH₃ | N | |
| Cl | H | H | CN | CH₃ | CH₃ | CH | |
| Cl | H | H | CO₂CH₃ | CH₃ | CH₃ | CH | |
| Cl | H | H | NO₂ | OCH₃ | OCH₃ | N | |
| Cl | 5-Cl | H | SO₂CH₃ | CH₃ | CH₃ | N | |
| CF₃ | H | H | CN | CH₃ | OCH₃ | CH | |
| CF₃ | H | H | CO₂C₂H₅ | CH₃ | CH₃ | N | |
| Br | H | H | CO₂CH₃ | OCH₃ | CH₃ | CH | |
| CH₃ | H | H | C(O)NH₂ | CH₃ | CH₃ | N | |
| CH₃ | 5-Cl | H | CN | CH₃ | CH₃ | CH | |

TABLE I-a-continued

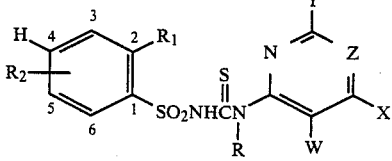

| R₁ | R₂ | R | W | X | Y | Z | m.p. (°C.) |
|---|---|---|---|---|---|---|---|
| n-C₃H₇ | H | H | CN | CH₃ | CH₃ | CH | |
| CH₂OCH₃ | H | H | CN | CH₃ | CH₃ | N | |
| CH₂OCH₃ | H | H | S(O)CH₃ | CH₃ | CH₃ | N | |
| CH₂CH₂OCH₃ | H | H | CO₂CH₃ | OCH₃ | CH₃ | CH | |
| SCF₃ | H | H | SO₂CH₃ | CH₃ | CH₃ | N | |
| SCF₂H | H | H | NO₂ | OCH₃ | CH₃ | CH | |
| SCF₂H | 5-CH₃ | H | CN | OCH₃ | CH₃ | N | |
| Cl | H | H | CO₂C₂H₅ | CH₃ | CH₃ | CH | |

TABLE II-a

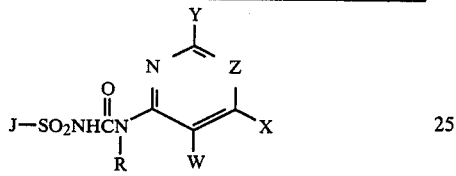

wherein J-2 is as defined above

| J | R | R₃ | W | X | Y | Z | m.p. (°C.) |
|---|---|---|---|---|---|---|---|
| J-2 | H | Cl | CN | CH₃ | CH₃ | N | |
| J-2 | H | Cl | CN | CH₃ | CH₃ | CH | 178–180(d) |
| J-2 | H | SO₂CH₃ | CO₂CH₃ | CH₃ | CH₃ | CH | |
| J-2 | H | SO₂N(CH₃)₂ | NO₂ | OCH₃ | OCH₃ | N | |
| J-2 | H | SO₂CH₃ | SO₂CH₃ | CH₃ | CH₃ | N | |

TABLE II-a-continued

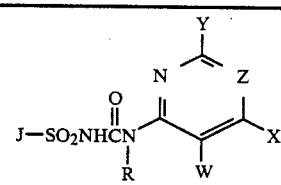

wherein J-2 is as defined above

| J | R | R₃ | W | X | Y | Z | m.p. (°C.) |
|---|---|---|---|---|---|---|---|
| J-2 | H | SO₂N(CH₃)₂ | CN | OCH₃ | CH₃ | N | |

TABLE II-b

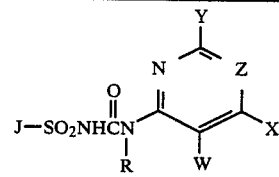

wherein J-3 is as defined above, m is 0 unless indicated by *, wherein m is 1, and R₁₆ is H.

| J | R | R₄ | R₅ | Q | W | X | Y | Z | m.p. (°C.) |
|---|---|---|---|---|---|---|---|---|---|
| J-3 | H | H | H | O | CN | CH₃ | CH₃ | CH | |
| J-3 | H | H | CH₃ | O | CO₂CH₃ | CH₃ | CH₃ | N | |
| J-3 | H | CH₃ | CH₃ | O | CN | CH₃ | CH₃ | N | |
| J-3 | H | CH₃ | CH₃ | S | CO₂CH₃ | CH₃ | CH₃ | CH | |
| J-3 | H | H | H | S | CN | OCH₃ | CH₃ | N | |
| J-3 | H | H | CH₃ | S | CN | OCH₃ | OCH₃ | CH | |
| J-3 | H | CH₃ | CH₃ | SO₂ | CO₂CH₃ | CH₃ | CH₃ | CH | |
| J-3 | H | CH₃ | H | SO₂ | CN | CH₃ | CH₃ | N | |
| J-3 | H | CH₃ | H | SO₂ | NO₂ | OCH₃ | OCH₃ | N | |
| J-3 | H | H | C₃H₇ | SO₂ | CN | CH₃ | CH₃ | CH | |
| J-3 | H | CH₃ | H | O | CN | CH₃ | CH₃ | CH | 180–183 |
| J-3 | H | CH₃ | CH₃ | O | CN | CH₃ | CH₃ | CH | 185–187 |
| J-3* | H | H | H | O | CN | CH₃ | CH₃ | CH | |
| J-3* | H | H | CH₃ | O | CO₂CH₃ | CH₃ | CH₃ | N | |
| J-3* | H | CH₃ | CH₃ | O | CN | CH₃ | CH₃ | N | |
| J-3* | H | CH₃ | CH₃ | S | CO₂CH₃ | CH₃ | CH₃ | CH | |
| J-3* | H | H | H | S | CN | OCH₃ | CH₃ | N | |
| J-3* | H | H | CH₃ | S | CN | OCH₃ | OCH₃ | CH | |
| J-3* | H | CH₃ | CH₃ | SO₂ | CO₂CH₃ | CH₃ | CH₃ | CH | |
| J-3* | H | CH₃ | H | SO₂ | CN | CH₃ | CH₃ | N | |
| J-3* | H | CH₃ | H | SO₂ | NO₂ | OCH₃ | OCH₃ | N | |
| J-3* | H | H | C₃H₇ | SO₂ | CN | CH₃ | CH₃ | CH | |
| J-3* | H | CH₃ | H | O | CN | CH₃ | CH₃ | CH | |
| J-3* | H | CH₃ | CH₃ | O | CN | CH₃ | CH₃ | CH | |

TABLE II-c

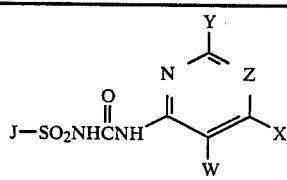

wherein J-4 is as defined above, m is 0 unless indicated by *, wherein m is 1 and $R_{16}$ is H.

| J | $R_{17}$ | W | X | Y | Z | m.p. (°C.) |
|---|---|---|---|---|---|---|
| J-4 | n-$C_4H_9$ | CN | $CH_3$ | $CH_3$ | CH | |
| J-4 | n-$C_4H_9$ | $CO_2CH_3$ | $CH_3$ | $CH_3$ | N | |
| J-4 | $CH_2CH_2F$ | $NO_2$ | $OCH_3$ | $OCH_3$ | CH | |
| J-4 | $CH_2CH_2OCH_3$ | CN | $CH_3$ | $CH_3$ | N | |
| J-4 | $CO_2C_2H_5$ | $CO_2CH_3$ | $CH_3$ | $CH_3$ | CH | |
| J-4* | n-$C_4H_9$ | CN | $CH_3$ | $CH_3$ | CH | |
| J-4* | $CH_3$ | $CO_2CH_3$ | $CH_3$ | $CH_3$ | N | |
| J-4* | H | $NO_2$ | $OCH_3$ | $OCH_3$ | CH | |
| J-4* | $CH_2CH_3$ | CN | $CH_3$ | $CH_3$ | N | |
| J-4* | $CH_2CH_2CH_3$ | $CO_2CH_3$ | $CH_3$ | $CH_3$ | CH | |

TABLE II-d

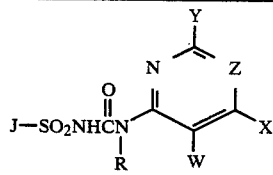

wherein J-5 and J-6 are as defined above

| J | R | $R_6$ | W | X | Y | Z | m.p. (°C.) |
|---|---|---|---|---|---|---|---|
| J-5 | H | $CO_2CH_3$ | CN | $CH_3$ | $CH_3$ | CH | 196–200(d) |
| J-5 | H | $CO_2CH_3$ | $CO_2CH_3$ | $CH_3$ | $CH_3$ | CH | |
| J-6 | H | Br | CN | $CH_3$ | $CH_3$ | N | |
| J-5 | H | Br | $SO_2CH_3$ | $CH_3$ | $CH_3$ | N | |
| J-5 | H | Cl | CN | $OCH_3$ | $CH_3$ | N | |
| J-6 | H | $SO_2CH_3$ | $NO_2$ | $OCH_3$ | $OCH_3$ | N | |
| J-5 | H | $SCH_3$ | $CO_2CH_3$ | $CH_3$ | $OCH_3$ | N | |
| J-5 | H | $SO_2C_3H_7$-n | CN | $CH_3$ | $CH_3$ | CH | |
| J-5 | H | $CO_2C_3H_7$-i | CN | $CH_3$ | $CH_3$ | CH | |
| J-6 | H | $CO_2CH_3$ | CN | $CH_3$ | $CH_3$ | N | |

TABLE II-d-continued

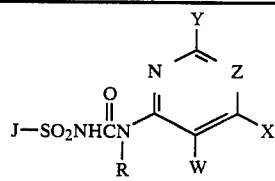

wherein J-5 and J-6 are as defined above

| J | R | $R_6$ | W | X | Y | Z | m.p. (°C.) |
|---|---|---|---|---|---|---|---|
| J-6 | H | $CO_2CH_3$ | $CO_2CH_3$ | $CH_3$ | $CH_3$ | CH | |

TABLE II-e

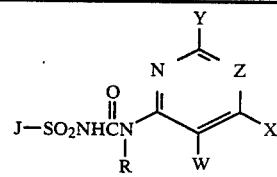

wherein J-7 is as defined above

| J | R | $R_7$ | W | X | Y | Z | m.p. (°C.) |
|---|---|---|---|---|---|---|---|
| J-7 | H | $CH_3$ | CN | $CH_3$ | $CH_3$ | CH | |
| J-7 | H | $C_2H_7$-n | CN | $CH_3$ | $CH_3$ | N | |
| J-7 | H | $OCH_3$ | $CO_2CH_3$ | $CH_3$ | $CH_3$ | CH | |
| J-7 | H | $OC_3H_7$-i | $CO_2CH_3$ | $CH_3$ | $CH_3$ | N | |
| J-7 | H | $SO_2CH_3$ | $SO_2CH_3$ | $CH_3$ | $CH_3$ | N | |
| J-7 | H | $SC_2H_5$ | $NO_2$ | $OCH_3$ | $OCH_3$ | N | |
| J-7 | H | $OSO_2C_3H_7$-n | CN | $CH_3$ | $CH_3$ | CH | |
| J-7 | H | Cl | CN | $OCH_3$ | $CH_3$ | CH | |
| J-7 | H | Cl | $CO_2CH_3$ | $CH_3$ | $CH_3$ | CH | |

TABLE II-f

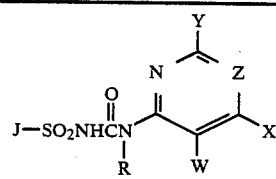

wherein J-8 is as defined above

| J | R | m | W | X | Y | Z | $R_{16}$ | $R_{18}$ | m.p. (°C.) |
|---|---|---|---|---|---|---|---|---|---|
| J-8 | H | 0 | CN | $CH_3$ | $CH_3$ | CH | H | H | |
| J-8 | H | 0 | CN | $CH_3$ | $CH_3$ | N | H | H | |
| J-8 | H | 0 | $CO_2CH_3$ | $CH_3$ | $CH_3$ | N | H | H | |
| J-8 | H | 0 | CN | $OCH_3$ | $CH_3$ | N | H | H | |
| J-8 | H | 0 | $NO_2$ | $OCH_3$ | $OCH_3$ | CH | H | H | |
| J-8 | H | 1 | $NO_2$ | $CH_3$ | $CH_3$ | N | H | H | |
| J-8 | H | 1 | CN | $CH_3$ | $CH_3$ | CH | H | $CH_3$ | |
| J-8 | H | 1 | CN | $OCH_3$ | $CH_3$ | N | H | $CH_3$ | |
| J-8 | H | 1 | $SO_2CH_3$ | $OCH_3$ | $CH_3$ | CH | H | H | |
| J-8 | H | 1 | CN | $CH_3$ | $CH_3$ | CH | H | H | 212–215(d) |
| J-8 | H | 1 | $SO_2CH_3$ | $CH_3$ | $CH_3$ | N | H | H | |
| J-8 | H | 1 | $NO_2$ | $OCH_3$ | $OCH_3$ | N | H | H | |
| J-8 | H | 1 | $NO_2$ | Cl | $OCH_3$ | CH | H | H | |
| J-8 | H | 1 | CN | $CH_3$ | $CH_3$ | N | H | H | |
| J-8 | H | 1 | $CO_2CH_3$ | $CH_3$ | $CH_3$ | CH | H | H | |

TABLE II-g

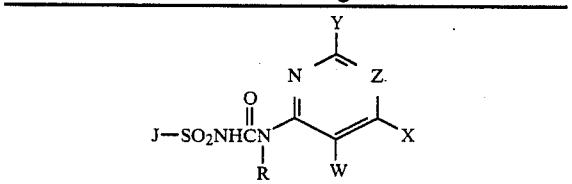

wherein J-9 is as defined above

| J | R | R$_8$ | W | X | Y | Z | m.p. (°C.) |
|---|---|---|---|---|---|---|---|
| J-9 | H | CH$_3$ | CN | CH$_3$ | CH$_3$ | CH | |
| J-9 | H | CH$_3$ | CN | CH$_3$ | CH$_3$ | N | |
| J-9 | H | C$_2$H$_5$ | CO$_2$CH$_3$ | CH$_3$ | CH$_3$ | CH | |
| J-9 | H | CH$_3$ | CN | OCH$_3$ | CH$_3$ | N | |

TABLE II-g-continued

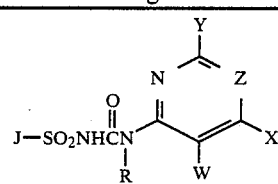

wherein J-9 is as defined above

| J | R | R$_8$ | W | X | Y | Z | m.p. (°C.) |
|---|---|---|---|---|---|---|---|
| J-9 | H | CH$_3$ | NO$_2$ | OCH$_3$ | OCH$_3$ | N | |
| J-9 | H | CH$_2$CH$_2$CH$_3$ | CN | CH$_3$ | CH$_3$ | CH | |
| J-9 | H | CH$_3$ | CN | CH$_3$ | OCH$_3$ | CH | |

TABLE II-h

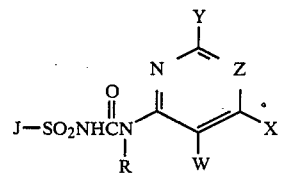

wherein J-10 is as defined above

| J | R | R$_{20}$ | W | X | Y | Z | R$_{19}$ | R$_{21}$ | m.p. (°C.) |
|---|---|---|---|---|---|---|---|---|---|
| J-10 | H | CO$_2$CH$_3$ | CN | CH$_3$ | CH$_3$ | CH | CH$_3$ | H | |
| J-10 | H | CO$_2$CH$_3$ | CO$_2$CH$_3$ | CH$_3$ | CH$_3$ | CH | CH$_3$ | H | |
| J-10 | H | Br | CN | CH$_3$ | CH$_3$ | N | CH$_3$ | H | |
| J-10 | H | Br | SO$_2$CH$_3$ | CH$_3$ | CH$_3$ | N | CH$_3$ | Cl | |
| J-10 | H | Cl | CN | OCH$_3$ | CH$_3$ | N | CH$_3$ | H | |
| J-10 | H | SO$_2$CH$_3$ | NO$_2$ | OCH$_3$ | OCH$_3$ | N | CH$_3$ | H | |
| J-10 | H | OCF$_2$H | CO$_2$CH$_3$ | CH$_3$ | OCH$_3$ | N | CH$_3$ | CH$_3$ | |
| J-10 | H | SO$_2$C$_3$H$_7$-n | CN | CH$_3$ | CH$_3$ | CH | C$_2$H$_5$ | H | |
| J-10 | H | CO$_2$C$_3$H$_7$-i | CN | CH$_3$ | CH$_3$ | CH | CH$_3$ | H | |
| J-10 | H | CO$_2$CH$_3$ | CN | CH$_3$ | CH$_3$ | N | CH$_3$ | H | |
| J-10 | H | CO$_2$CH$_3$ | CO$_2$CH$_3$ | CH$_3$ | CH$_3$ | CH | phenyl | H | |

TABLE II-i

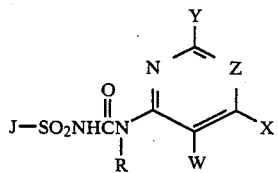

wherein J-11 is as defined above

| J | R | R$_{20}$ | W | X | Y | Z | R$_{19}$ | R$_{21}$ | m.p. (°C.) |
|---|---|---|---|---|---|---|---|---|---|
| J-11 | H | CO$_2$CH$_3$ | CN | CH$_3$ | CH$_3$ | CH | CH$_3$ | H | |
| J-11 | H | CO$_2$CH$_3$ | CO$_2$CH$_3$ | CH$_3$ | CH$_3$ | CH | CH$_3$ | H | |
| J-11 | H | Br | CN | CH$_3$ | CH$_3$ | N | CH$_3$ | H | |
| J-11 | H | Br | SO$_2$CH$_3$ | CH$_3$ | CH$_3$ | N | CH$_3$ | Cl | |
| J-11 | H | Cl | CN | OCH$_3$ | CH$_3$ | N | CH$_3$ | H | |
| J-11 | H | SO$_2$CH$_3$ | NO$_2$ | OCH$_3$ | OCH$_3$ | N | CH$_3$ | H | |
| J-11 | H | OCF$_2$H | CO$_2$CH$_3$ | CH$_3$ | OCH$_3$ | N | CH$_3$ | CH$_3$ | |
| J-11 | H | SO$_2$C$_3$H$_7$-n | CN | CH$_3$ | CH$_3$ | CH | C$_2$H$_5$ | H | |
| J-11 | H | CO$_2$C$_3$H$_7$-i | CN | CH$_3$ | CH$_3$ | CH | CH$_3$ | H | |
| J-11 | H | CO$_2$CH$_3$ | CN | CH$_3$ | CH$_3$ | N | CH$_3$ | H | |
| J-11 | H | CO$_2$CH$_3$ | CO$_2$CH$_3$ | CH$_3$ | CH$_3$ | CH | phenyl | H | |

TABLE II-j

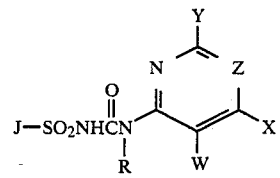

wherein J-12 is as defined above

| J | R | $R_{20}$ | W | X | Y | Z | $R_{19}$ | $R_{21}$ | m.p. (°C.) |
|---|---|---|---|---|---|---|---|---|---|
| J-12 | H | $CO_2CH_3$ | CN | $CH_3$ | $CH_3$ | CH | $CH_3$ | H | |
| J-12 | H | $CO_2CH_3$ | $CO_2CH_3$ | $CH_3$ | $CH_3$ | CH | $CH_3$ | H | |
| J-12 | H | Br | CN | $CH_3$ | $CH_3$ | N | $CH_3$ | H | |
| J-12 | H | Br | $SO_2CH_3$ | $CH_3$ | $CH_3$ | N | $CH_3$ | Cl | |
| J-12 | H | Cl | CN | $OCH_3$ | $CH_3$ | N | $CH_3$ | H | |
| J-12 | H | $SO_2CH_3$ | $NO_2$ | $OCH_3$ | $OCH_3$ | N | $CH_3$ | H | |
| J-12 | H | $OCF_2H$ | $CO_2CH_3$ | $CH_3$ | $OCH_3$ | N | $CH_3$ | $CH_3$ | |
| J-12 | H | $SO_2C_3H_7$—n | CN | $CH_3$ | $CH_3$ | CH | $C_2H_5$ | H | |
| J-12 | H | $CO_2C_3H_7$—i | CN | $CH_3$ | $CH_3$ | CH | $CH_3$ | H | |
| J-12 | H | $CO_2CH_3$ | CN | $CH_3$ | $CH_3$ | N | $CH_3$ | H | |
| J-12 | H | $CO_2CH_3$ | $CO_2CH_3$ | $CH_3$ | $CH_3$ | CH | phenyl | H | |

TABLE II-k

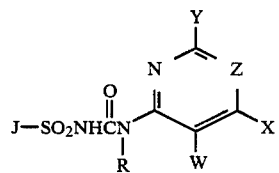

wherein J-13 is as defined above

| J | R | $R_{20}$ | W | X | Y | Z | $R_{19}$ | $R_{21}$ | m.p. (°C.) |
|---|---|---|---|---|---|---|---|---|---|
| J-13 | H | $CO_2CH_3$ | CN | $CH_3$ | $CH_3$ | CH | $CH_3$ | H | |
| J-13 | H | $CO_2CH_3$ | $CO_2CH_3$ | $CH_3$ | $CH_3$ | CH | $CH_3$ | H | |
| J-13 | H | Br | CN | $CH_3$ | $CH_3$ | N | $CH_3$ | H | |
| J-13 | H | Br | $SO_2CH_3$ | $CH_3$ | $CH_3$ | N | $CH_3$ | Cl | |
| J-13 | H | Cl | CN | $OCH_3$ | $CH_3$ | N | $CH_3$ | H | |
| J-13 | H | $SO_2CH_3$ | $NO_2$ | $OCH_3$ | $OCH_3$ | N | $CH_3$ | H | |
| J-13 | H | $OCF_2H$ | $CO_2CH_3$ | $CH_3$ | $OCH_3$ | N | $CH_3$ | $CH_3$ | |
| J-13 | H | $SO_2C_3H_7$—n | CN | $CH_3$ | $CH_3$ | CH | $C_2H_5$ | H | |
| J-13 | H | $CO_2C_3H_7$—i | CN | $CH_3$ | $CH_3$ | CH | $CH_3$ | H | |
| J-13 | H | $CO_2CH_3$ | CN | $CH_3$ | $CH_3$ | N | $CH_3$ | H | |
| J-13 | H | $CO_2CH_3$ | $CO_2CH_3$ | $CH_3$ | $CH_3$ | CH | phenyl | H | |

TABLE II-l

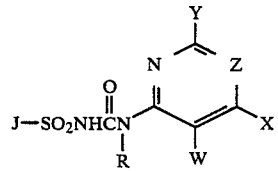

wherein J-14 is as defined above

| J | R | $R_6$ | W | X | Y | Z | m.p. (°C.) |
|---|---|---|---|---|---|---|---|
| J-14 | H | $CO_2CH_3$ | CN | $CH_3$ | $CH_3$ | CH | |
| J-14 | H | $CO_2CH_3$ | $CO_2CH_3$ | $CH_3$ | $CH_3$ | CH | |
| J-14 | H | Br | $SO_2CH_3$ | $CH_3$ | $CH_3$ | N | |
| J-14 | H | Cl | CN | $OCH_3$ | $CH_3$ | N | |
| J-14 | H | $SCH_3$ | $CO_2CH_3$ | $CH_3$ | $OCH_3$ | N | |
| J-14 | H | $SO_2C_3H_7$—n | CN | $CH_3$ | $CH_3$ | CH | |
| J-14 | H | $CO_2C_3H_7$—i | CN | $CH_3$ | $CH_3$ | CH | |

TABLE II-m

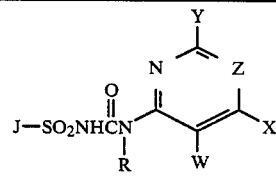

wherein J-15 is as defined above

| J | R | $R_3$ | W | X | Y | Z | m.p. (°C.) |
|---|---|---|---|---|---|---|---|
| J-15 | H | Cl | CN | $CH_3$ | $CH_3$ | N | |
| J-15 | H | Cl | CN | $CH_3$ | $CH_3$ | CH | |
| J-15 | H | $SO_2CH_3$ | $CO_2CH_3$ | $CH_3$ | $CH_3$ | CH | |
| J-15 | H | $SO_2N(CH_3)_2$ | $NO_2$ | $OCH_3$ | $OCH_3$ | N | |
| J-15 | H | $SO_2CH_3$ | $SO_2CH_3$ | $CH_3$ | $CH_3$ | N | |
| J-15 | H | $SO_2N(CH_3)_2$ | CN | $OCH_3$ | $CH_3$ | N | |

TABLE II-n

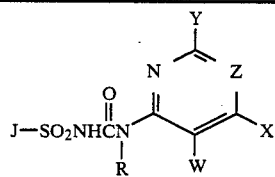

wherein J-16 is as defined above, m is 0 unless indicated by *, wherein m is 1, $R_{16}$ is H and $R_{22}$ is $CH_3$.

| J | R | W | X | Y | Z | m.p. (°C.) |
|---|---|---|---|---|---|---|
| J-16 | H | CN | $CH_3$ | $CH_3$ | CH | |
| J-16 | H | $CO_2CH_3$ | $CH_3$ | $CH_3$ | N | |
| J-16 | H | $NO_2$ | $OCH_3$ | $OCH_3$ | CH | |
| J-16 | H | CN | $CH_3$ | $CH_3$ | N | |
| J-16 | H | $CO_2CH_3$ | $CH_3$ | $CH_3$ | CH | |
| J-16* | H | CN | $CH_3$ | $CH_3$ | CH | |
| J-16* | H | $CO_2CH_3$ | $CH_3$ | $CH_3$ | N | |
| J-16* | H | $NO_2$ | $OCH_3$ | $OCH_3$ | CH | |
| J-16* | H | CN | $CH_3$ | $CH_3$ | N | |
| J-16* | H | $CO_2CH_3$ | $CH_3$ | $CH_3$ | CH | |

TABLE II-o

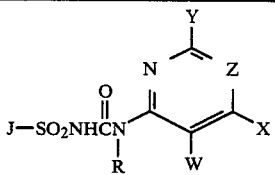

wherein J-17 is as defined above, m is 0 unless indicated by *, wherein m is 1 and $R_{16}$ is H.

| J | R | $R_{23}$ | $R_{24}$ | W | X | Y | Z | m.p. (°C.) |
|---|---|---|---|---|---|---|---|---|
| J-17 | H | H | H | CN | $CH_3$ | $CH_3$ | CH | |
| J-17 | H | H | Cl | $CO_2CH_3$ | $CH_3$ | $CH_3$ | N | |
| J-17 | H | Cl | Cl | CN | $CH_3$ | $CH_3$ | N | |
| J-17 | H | Cl | Cl | $CO_2CH_3$ | $CH_3$ | $CH_3$ | CH | |
| J-17 | H | H | H | CN | $OCH_3$ | $CH_3$ | N | |
| J-17 | H | H | Cl | CN | $OCH_3$ | $OCH_3$ | CH | |
| J-17 | H | Cl | H | CN | $CH_3$ | $CH_3$ | N | |
| J-17 | H | Cl | H | $NO_2$ | $OCH_3$ | $OCH_3$ | N | |
| J-17 | H | Cl | H | CN | $CH_3$ | $CH_3$ | CH | |
| J-17 | H | Cl | Cl | CN | $CH_3$ | $CH_3$ | CH | |
| J-17* | H | H | H | CN | $CH_3$ | $CH_3$ | CH | |
| J-17* | H | H | Cl | $CO_2CH_3$ | $CH_3$ | $CH_3$ | N | |
| J-17* | H | Cl | Cl | CN | $CH_3$ | $CH_3$ | N | |
| J-17* | H | Cl | Cl | $CO_2CH_3$ | $CH_3$ | $CH_3$ | CH | |
| J-17* | H | H | H | CN | $OCH_3$ | $CH_3$ | N | |
| J-17* | H | H | Cl | CN | $OCH_3$ | $OCH_3$ | CH | |
| J-17* | H | Cl | H | CN | $CH_3$ | $CH_3$ | N | |
| J-17* | H | Cl | H | $NO_2$ | $OCH_3$ | $OCH_3$ | N | |
| J-17* | H | Cl | H | CN | $CH_3$ | $CH_3$ | CH | |
| J-17* | H | Cl | Cl | CN | $CH_3$ | $CH_3$ | CH | |

TABLE III-a

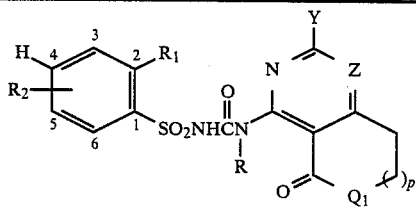

| $R_1$ | $R_2$ | R | $Q_1$ | p | Y | Z | m.p. (°C.) |
|---|---|---|---|---|---|---|---|
| $NO_2$ | H | H | O | 0 | $CH_3$ | CH | |
| $NO_2$ | H | H | O | 0 | $CH_3$ | N | |
| $NO_2$ | H | H | $NCH_3$ | 0 | $CH_3$ | CH | |
| $NO_2$ | 5-Cl | H | $NCH_3$ | 1 | $CH_3$ | N | |
| $CO_2CH_3$ | H | H | $CH_2$ | 0 | $CH_3$ | CH | |

TABLE III-a-continued

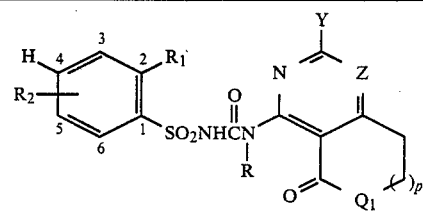

| $R_1$ | $R_2$ | R | $Q_1$ | p | Y | Z | m.p. (°C.) |
|---|---|---|---|---|---|---|---|
| $CO_2CH_3$ | H | $CH_3$ | $CH_2$ | 0 | $CH_3$ | N | |
| Cl | H | H | O | 0 | $CH_3$ | N | |
| Cl | H | H | O | 1 | $CH_3$ | N | |
| Cl | H | H | O | 0 | $CH_3$ | CH | |
| Cl | H | H | $NCH_3$ | 0 | $CH_3$ | CH | |
| $CO_2CH_3$ | 5-$OCH_3$ | H | O | 1 | $OCH_3$ | N | |
| Cl | 5-Cl | H | $CH_2$ | 0 | $CH_3$ | N | |
| $SO_2N(CH_3)_2$ | H | H | O | 0 | $OCH_3$ | CH | |
| $CF_3$ | H | H | $NCH_3$ | 0 | $CH_3$ | N | |
| $CO_2CH_3$ | H | H | $NCH_3$ | 1 | $CH_3$ | CH | |
| $CH_3$ | 5-Cl | H | O | 0 | $CH_3$ | CH | |
| $CO_2C_2H_5$ | H | H | O | 0 | $CH_3$ | CH | |
| $CH_2OCH_3$ | H | H | O | 0 | $CH_3$ | N | |
| $CH_2OCH_3$ | H | H | $CH_2$ | 0 | $CH_3$ | N | |
| $SO_2CH_3$ | H | H | $NCH_3$ | 1 | $CH_3$ | CH | |
| $SCF_2H$ | H | H | $CH_2$ | 0 | $CH_3$ | N | |
| $OCH_2CH_3$ | H | H | O | 1 | $CH_3$ | CH | |
| $SCF_2H$ | 5-$CH_3$ | H | O | 1 | $CH_3$ | N | |
| $SO_2N(CH_3)_2$ | H | H | $NCH_3$ | 0 | $CH_3$ | CH | |

TABLE III-b

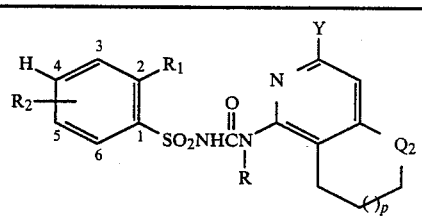

| $R_1$ | $R_2$ | R | $Q_1$ | p | Y | m.p. (°C.) |
|---|---|---|---|---|---|---|
| $NO_2$ | H | H | O | 0 | $CH_3$ | |
| $NO_2$ | H | H | O | 0 | $OCH_3$ | |
| $NO_2$ | H | H | $NCH_3$ | 0 | $CH_3$ | |
| $NO_2$ | 5-Cl | H | $NCH_3$ | 1 | $CH_3$ | |
| $CO_2CH_3$ | H | H | $CH_2$ | 0 | $CH_3$ | |
| $CO_2CH_3$ | H | $CH_3$ | $CH_2$ | 0 | $CH_3$ | |
| Cl | H | H | O | 0 | $CH_3$ | |
| Cl | H | H | O | 1 | $CH_3$ | |
| Cl | H | H | O | 0 | $CH_3$ | |
| Cl | H | H | $NCH_3$ | 0 | $CH_3$ | |
| $CO_2CH_3$ | 5-$OCH_3$ | H | O | 1 | $OCH_3$ | |
| Cl | 5-Cl | H | $CH_2$ | 0 | $CH_3$ | |
| $SO_2N(CH_3)_2$ | H | H | O | 0 | $OCH_3$ | |
| $CF_3$ | H | H | $NCH_3$ | 0 | $CH_3$ | |
| $CO_2CH_3$ | H | H | $NCH_3$ | 1 | $CH_3$ | |
| $CH_3$ | 5-Cl | H | O | 0 | $CH_3$ | |
| $CO_2C_2H_5$ | H | H | O | 0 | $CH_3$ | |
| $CH_2OCH_3$ | H | H | O | 0 | $CH_3$ | |
| $CH_2OCH_3$ | H | H | $CH_2$ | 0 | $CH_3$ | |
| $SO_2CH_3$ | H | H | $NCH_3$ | 1 | $CH_3$ | |
| $SCF_2H$ | H | H | $CH_2$ | 0 | $CH_3$ | |
| $OCH_2CH_3$ | H | H | O | 1 | $CH_3$ | |
| $SCF_2H$ | 5-$CH_3$ | H | O | 1 | $CH_3$ | |
| $SO_2N(CH_3)_2$ | H | H | $NCH_3$ | 0 | $CH_3$ | |

TABLE III-c

| R₁ | R₂ | R | Q₃ | p | Y | Z | m.p. (°C.) |
|---|---|---|---|---|---|---|---|
| $NO_2$ | H | H | O | 0 | $CH_3$ | CH | |
| $NO_2$ | H | H | SO | 0 | $CH_3$ | CH | |
| $CO_2CH_3$ | 5-$OCH_3$ | H | SO | 1 | $CH_3$ | N | |
| $CO_2CH_3$ | H | H | $SO_2$ | 0 | $CH_3$ | CH | |
| $CO_2CH_3$ | H | $CH_3$ | $SO_2$ | 0 | $CH_3$ | N | |
| Cl | H | H | O | 0 | $CH_3$ | CH | |
| Cl | H | H | SO | 0 | $CH_3$ | CH | |
| Cl | 5-Cl | H | $SO_2$ | 0 | $CH_3$ | N | |
| $SO_2N(CH_3)_2$ | H | H | O | 0 | $OCH_3$ | CH | |

TABLE III-c-continued

| R₁ | R₂ | R | Q₃ | p | Y | Z | m.p. (°C.) |
|---|---|---|---|---|---|---|---|
| $CF_3$ | H | $CH_3$ | SO | 0 | $CH_3$ | N | |
| $CO_2CH_3$ | H | H | SO | 1 | $CH_3$ | CH | |
| $CO_2CH_3$ | 5-$CH_3$ | H | O | 0 | $CH_3$ | CH | |
| $CO_2C_2H_5$ | H | H | O | 0 | $CH_3$ | CH | |
| $CH_2OCH_3$ | H | $CH_3$ | $SO_2$ | 0 | $CH_3$ | N | |
| $SO_2CH_3$ | H | H | SO | 1 | $CH_3$ | CH | |
| $OCH_2CH_3$ | H | H | $SO_2$ | 0 | $CH_3$ | N | |
| $SCF_2H$ | H | $CH_3$ | O | 1 | $CH_3$ | CH | |
| $SO_2N(CH_3)_2$ | H | $CH_3$ | SO | 0 | $CH_3$ | CH | |

TABLE III-d

| J | | p | Q₁ | Y | Z | m.p. (°C.) |
|---|---|---|---|---|---|---|
| J-2 | ($R_3$ = Cl) | 0 | O | $CH_3$ | CH | |
| J-3 | (Q = O, $R_0$ = $R_5$ = H, m = 1, $R_{16}$ = H) | 0 | O | $CH_3$ | CH | |
| J-3 | (Q = $SO_2$, $R_4$ = $CH_3$, $R_5$ = H, m = 0, $R_{16}$ = H) | 0 | O | $CH_3$ | CH | |
| J-3 | (Q = $SO_2$, $R_4$ = $R_5$ = $CH_3$, m = 0, $R_{16}$ = H) | 0 | O | $CH_3$ | CH | |
| J-4 | ($R_{17}$ = H, m = 0, $R_{16}$ = H) | 0 | O | $CH_3$ | CH | |
| J-4 | ($R_{17}$ = $CH_3$, m = 0, $R_{16}$ = H) | 0 | O | $CH_3$ | CH | |
| J-4 | ($R_{17}$ = n-$C_4H_9$, m = 0, $R_{16}$ = H) | 0 | O | $CH_3$ | CH | |
| J-4 | ($R_{17}$ = H, m = 0, $R_{16}$ = H) | 1 | O | $CH_3$ | CH | |
| J-4 | ($R_{17}$ = H, m = 0; $R_{16}$ = H) | 0 | $NCH_3$ | $CH_3$ | CH | |
| J-4 | ($R_{17}$ = H, m = 0, $R_{16}$ = H) | 0 | O | $CH_3$ | N | |
| J-5 | ($R_6$ = $CO_2CH_3$) | 0 | O | $CH_3$ | CH | |
| J-6 | ($R_6$ = $CO_2CH_3$) | 0 | O | $CH_3$ | CH | |
| J-6 | ($R_6$ = $CO_2CH_3$) | 0 | O | $CH_3$ | N | |
| J-6 | ($R_6$ = $CO_2CH_3$) | 1 | O | $CH_3$ | CH | |
| J-6 | ($R_6$ = $CO_2CH_3$) | 0 | $NCH_3$ | $CH_3$ | CH | |
| J-7 | ($R_7$ = Cl) | 0 | O | $CH_3$ | CH | |
| J-8 | (m = 0, $R_{16}$ = H) | 0 | O | $CH_3$ | CH | |
| J-8 | (m = 0, $R_{16}$ = H) | 0 | O | $CH_3$ | N | |
| J-8 | (m = 1, $R_{18}$ = $CH_3$, $R_{16}$ = H) | 0 | O | $CH_3$ | CH | |
| J-9 | ($R_8$ = $CH_3$) | 0 | O | $CH_3$ | CH | |
| J-10 | ($R_{19}$ = $CH_3$, $R_{20}$ = $CO_2CH_3$, $R_{21}$ = H) | 0 | O | $CH_3$ | CH | |
| J-10 | ($R_{19}$ = $CH_3$, $R_{20}$ = Br, $R_{21}$ = H) | 0 | O | $CH_3$ | CH | |
| J-11 | ($R_{19}$ = $CH_3$, $R_{20}$ = $CO_2CH_3$, $R_{21}$ = H) | 0 | O | $CH_3$ | CH | |
| J-12 | ($R_{19}$ = $CH_3$, $R_{20}$ = $CO_2CH_3$, $R_{21}$ = H) | 0 | O | $CH_3$ | CH | |
| J-13 | ($R_{19}$ = $CH_3$, $R_{20}$ = $CO_2CH_3$, $R_{21}$ = H) | 0 | O | $CH_3$ | CH | |
| J-14 | ($R_6$ = $CO_2CH_3$) | 0 | O | $CH_3$ | CH | |
| J-15 | ($R_3$ = $SO_2CH_3$) | 0 | O | CH | CH | |
| J-16 | (m = 0, $R_{22}$ = $CH_3$, $R_{16}$ = H) | 0 | O | $CH_3$ | CH | |
| J-16 | (m = 0, $R_{22}$ = $CH_3$, $R_{16}$ = H) | 1 | 0 | $CH_3$ | CH | |
| J-17 | (m = 0, $R_{23}$ = $R_{24}$ = H, $R_{16}$ = H) | 0 | O | $CH_3$ | CH | |
| J-17 | (m = 0, $R_{23}$ = $R_{24}$ = H, $R_{16}$ = H) | 1 | O | $CH_3$ | CH | |
| J-17 | (m = 0, $R_{23}$ = $R_{24}$ = H, $R_{16}$ = H) | 0 | $NCH_3$ | $CH_3$ | CH | |
| J-17 | (m = 0, $R_{23}$ = $R_{24}$ = Cl, $R_{16}$ = H) | 0 | O | $CH_3$ | CH | |

TABLE III-e

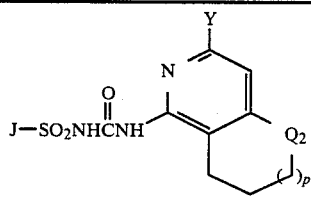

| J | | p | Q₂ | Y | m.p. (°C.) |
|---|---|---|----|---|------------|
| J-2 | ($R_3$ = Cl) | 0 | O | $CH_3$ | |
| J-3 | (Q = O, $R_4$ = $R_5$ = H, m = 1, $R_{16}$ = H) | 0 | O | $CH_3$ | |
| J-3 | (Q = $SO_2$, $R_4$ = $CH_3$, $R_5$ = H, m = 0, $R_{16}$ = H) | 0 | O | $CH_3$ | |
| J-3 | (Q = $SO_2$, $R_4$ = $R_5$ = $CH_3$, m = 0, $R_{16}$ = H) | 0 | O | $CH_3$ | |
| J-4 | ($R_{17}$ = H, m = 0, $R_{16}$ = H) | 0 | O | $CH_3$ | |
| J-4 | ($R_{17}$ = $CH_3$, m = 0, $R_{16}$ = H) | 0 | O | $CH_3$ | |
| J-4 | ($R_{17}$ n-$C_4H_9$, m = 0, $R_{16}$ = H) | 0 | O | $CH_3$ | |
| J-4 | ($R_{17}$ = H, m = 0, $R_{16}$ = H) | 1 | O | $CH_3$ | |
| J-4 | ($R_{17}$ = H, m = 0, $R_{16}$ = H) | 0 | $NCH_3$ | $CH_3$ | |
| J-4 | ($R_{17}$ = H, m = 0, $R_{16}$ = H) | 0 | O | $CH_3$ | |
| J-5 | ($R_6$ = $CO_2CH_3$) | 0 | O | $CH_3$ | |
| J-6 | ($R_6$ = $CO_2CH_3$) | 0 | O | $CH_3$ | |
| J-6 | ($R_6$ = $CO_2CH_3$) | 0 | O | $CH_3$ | |
| J-6 | ($R_6$ = $CO_2CH_3$) | 1 | O | $CH_3$ | |
| J-6 | ($R_6$ = $CO_2CH_3$) | 0 | $NCH_3$ | $CH_3$ | |
| J-7 | ($R_7$ = Cl) | 0 | O | $CH_3$ | |
| J-8 | (m = 0, $R_{16}$ = H) | 0 | O | $CH_3$ | |
| J-8 | (m = 0, $R_{16}$ = H) | 0 | O | $CH_3$ | |
| J-8 | (m = 1, $R_{18}$ = $CH_3$, $R_{16}$ = H) | 0 | O | $CH_3$ | |
| J-9 | ($R_8$ = $CH_3$) | 0 | O | $CH_3$ | |
| J-10 | ($R_{19}$ = $CH_3$, $R_{20}$ = $CO_2CH_3$, $R_{21}$ = H) | 0 | O | $CH_3$ | |
| J-10 | ($R_{19}$ = $CH_3$, $R_{20}$ = Br, $R_{21}$ = H) | 0 | O | $CH_3$ | |
| J-11 | ($R_{19}$ = $CH_3$, $R_{20}$ = $CO_2CH_3$, $R_{21}$ = H) | 0 | O | $CH_3$ | |
| J-12 | ($R_{19}$ = $CH_3$, $R_{20}$ = $CO_2CH_3$, $R_{21}$ = H) | 0 | O | $CH_3$ | |
| J-13 | ($R_{19}$ = $CH_3$, $R_{20}$ = $CO_2CH_3$, $R_{21}$ = H) | 0 | O | $CH_3$ | |
| J-14 | ($R_6$ = $CO_2CH_3$) | 0 | O | $CH_3$ | |
| J-15 | ($R_3$ = $SO_2CH_3$) | 0 | O | CH | |
| J-16 | (m = 0, $R_{22}$ = $CH_3$, $R_{16}$ = H) | 0 | O | $CH_3$ | |
| J-16 | (m = 0, $R_{22}$ = $CH_3$, $R_{16}$ = H) | 1 | O | $CH_3$ | |
| J-17 | (m = 0, $R_{23}$ = $R_{24}$ = H, $R_{16}$ = H) | 0 | O | $CH_3$ | |
| J-17 | (m = 0, $R_{23}$ = $R_{24}$ = H, $R_{16}$ = H) | 1 | O | $CH_3$ | |
| J-17 | (m = 0, $R_{23}$ = $R_{24}$ = H, $R_{16}$ = H) | 0 | $NCH_3$ | $CH_3$ | |
| J-17 | (m = 0, $R_{23}$ = $R_{24}$ = Cl, $R_{16}$ = H) | 0 | O | $CH_3$ | |

TABLE III-f

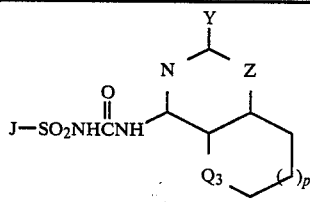

| J | | p | Q₃ | Y | Z | m.p. (°C.) |
|---|---|---|----|---|---|------------|
| J-2 | ($R_3$ = Cl) | 0 | O | $CH_3$ | CH | |
| J-3 | (Q = O, $R_4$ = $R_5$ = H, m = 1, $R_{16}$ = H) | 0 | O | $CH_3$ | CH | |
| J-3 | (Q = $SO_2$, $R_4$ = $CH_3$, $R_5$ = H, m = 0, $R_{16}$ = H) | 0 | O | $CH_3$ | CH | |
| J-3 | (Q = $SO_2$, $R_4$ = $R_5$ = $CH_3$, m = 0, $R_{16}$ = H) | 0 | O | $CH_3$ | CH | |
| J-4 | ($R_{17}$ = H, m = 0, $R_{16}$ = H) | 0 | O | $CH_3$ | CH | |
| J-4 | ($R_{17}$ = $CH_3$, m = 0, $R_{16}$ = H) | 0 | O | $CH_3$ | CH | |
| J-4 | ($R_{17}$ = n-$C_4H_9$, m = 0, $R_{16}$ = H) | 0 | O | $CH_3$ | CH | |
| J-4 | ($R_{17}$ = H, m = 0, $R_{16}$ = H) | 1 | O | $CH_3$ | CH | |
| J-4 | ($R_{17}$ = H, m = 0, $R_{16}$ = H) | 0 | $NCH_3$ | $CH_3$ | CH | |
| J-4 | ($R_{17}$ = H, m = 0, $R_{16}$ = H) | 0 | O | $CH_3$ | N | |
| J-5 | ($R_6$ = $CO_2CH_3$) | 0 | O | $CH_3$ | CH | |
| J-6 | ($R_6$ = $CO_2CH_3$) | 0 | O | $CH_3$ | CH | |
| J-6 | ($R_6$ = $CO_2CH_3$) | 0 | O | $CH_3$ | N | |
| J-6 | ($R_6$ = $CO_2CH_3$) | 1 | O | $CH_3$ | CH | |
| J-6 | ($R_6$ = $CO_2CH_3$) | 0 | $NCH_3$ | $CH_3$ | CH | |
| J-7 | ($R_7$ = Cl) | 0 | O | $CH_3$ | CH | |
| J-8 | (m = 0, $R_{16}$ = H) | 0 | O | $CH_3$ | CH | |
| J-8 | (m = 0, $R_{16}$ = H) | 0 | O | $CH_3$ | N | |
| J-8 | (m = 1, $R_{18}$ = $CH_3$, $R_{16}$ = H) | 0 | O | $CH_3$ | CH | |
| J-9 | ($R_8$ = $CH_3$) | 0 | O | $CH_3$ | CH | |

TABLE III-f-continued $$J-SO_2NHCNH \underset{Q_3}{\overset{O}{\|}} \underset{}{\overset{Y}{\underset{N}{\bigvee}}} Z$$

| J | | p | $Q_3$ | Y | Z | m.p. (°C.) |
|---|---|---|---|---|---|---|
| J-10 | ($R_{19}$ = $CH_3$, $R_{20}$ = $CO_2CH_3$, $R_{21}$ = H) | 0 | O | $CH_3$ | CH | |
| J-10 | ($R_{19}$ = $CH_3$, $R_{20}$ = Br, $R_{21}$ = H) | 0 | O | $CH_3$ | CH | |
| J-11 | ($R_{19}$ = $CH_3$, $R_{20}$ = $CO_2CH_3$, $R_{21}$ = H) | 0 | O | $CH_3$ | CH | |
| J-12 | ($R_{19}$ = $CH_3$, $R_{20}$ = $CO_2CH_3$, $R_{21}$ = H) | 0 | O | $CH_3$ | CH | |
| J-13 | ($R_{19}$ = $CH_3$, $R_{20}$ = $CO_2CH_3$, $R_{21}$ = H) | 0 | O | $CH_3$ | CH | |
| J-14 | ($R_6$ = $CO_2CH_3$) | 0 | 0 | $CH_3$ | CH | |
| J-15 | ($R_3$ = $SO_2CH_3$) | 0 | 0 | CH | CH | |
| J-16 | (m = 0, $R_{22}$ = $CH_3$, $R_{16}$ = H) | 0 | O | $CH_3$ | CH | |
| J-16 | (m = 0, $R_{22}$ = $CH_3$, $R_{16}$ = H) | 1 | O | $CH_3$ | CH | |
| J-17 | (m = 0, $R_{23}$ = $R_{24}$ = H, $R_{16}$ = H) | 0 | O | $CH_3$ | CH | |
| J-17 | (m = 0, $R_{23}$ = $R_{24}$ = H, $R_{16}$ = H) | 1 | O | $CH_3$ | CH | |
| J-17 | (m = 0, $R_{23}$ = $R_{24}$ = H, $R_{16}$ = H) | 0 | $NCH_3$ | $CH_3$ | CH | |
| J-17 | (m = 0, $R_{23}$ = $R_{24}$ = Cl, $R_{16}$ = H) | 0 | O | $CH_3$ | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Active Ingredient | Weight Percent | |
|---|---|---|---|
| | | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood. "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration". *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 6

Wettable Powder

| | |
|---|---|
| Methyl 2-[[(2-dimethylaminosulfonylphenyl)-sulfonylamino]carbonyl]-4,6-dimethylpyridin-3-carboxylate | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 7

Wettable Powder

| | |
|---|---|
| N'—[(3-cyano-4,6-dimethylpyridin-2-yl)-aminocarbonyl]-N,N—dimethyl-1,2-benzenedisulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 8

Granule

| | |
|---|---|
| Wettable powder of Example 7 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 9

Extruded Pellet

| | |
|---|---|
| Methyl 2-[[N—(2,6-dimethyl-5-nitropyrimidine-4-yl)aminocarbonyl]aminosulfonyl]benzoate | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 10

Oil Suspension

| | |
|---|---|
| Methyl 2-[[N—(3-cyano-4,6-dimethylpyridin-2-yl)-aminocarbonyl]aminosulfonyl]benzoate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 11

Wettable Powder

| | |
|---|---|
| Methyl 2-[[N—(2,6-dimethyl-5-nitropyrimidine-4-yl)aminocarbonyl]aminosulfonyl]benzoate | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 12

Low Strength Granule

| | |
|---|---|
| Methyl 2-[[N—(3-cyano-4,6-dimethylpyridin-2-yl)-aminocarbonyl]aminosulfonyl]benzoate | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 13

Aqueous Suspension

| | |
|---|---|
| N'—[(3-cyano-4,6-dimethylpyridin-2-yl)aminocarbonyl]-N,N—dimethyl-1,2-benzenedisulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 14

Solution

| | |
|---|---|
| Methyl 2-[[(2-dimethylaminosulfonylphenyl)sulfonylamino]carbonylamino]-4,6-dimethylpyridin-3-carboxylate, sodium salt | 5% |
| water | 95% |

The salt is added directly to the water with stirring to produce the solution, which may then be packaged for use.

EXAMPLE 15

Low Strength Granule

| | |
|---|---|
| Methyl 2-[[N—(2,6-dimethyl-5-nitropyrimidine-4-yl)-aminocarbonyl]aminosulfonyl]benzoate | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 16

Granule

| | |
|---|---|
| N'—[(3-cyano-4,6-dimethylpyridin-2-yl)aminocarbonyl]-N,N—dimethyl-1,2-benzenedisulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 17

High Strength Concentrate

| | |
|---|---|
| Methyl 2-[[(2-dimethylaminosulfonylphenyl)sulfonylamino]carbonylamino]-4,6-dimethylpyridin-3-carboxylate | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 18

Wettable Powder

| | |
|---|---|
| Methyl 2-[[(2-dimethylaminosulfonylphenyl)sulfonylamino]carbonylamino]-4,6-dimethylpyridin-3-carboxylate | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 19

Wettable Powder

| | |
|---|---|
| Methyl 2-[[N—(3-cyano-4,6-dimethylpyridin-2-yl)-aminocarbonyl]aminosulfonyl]benzoate | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 20

Oil Suspension

| | |
|---|---|
| N'—[(3-cyano-4,6-dimethylpyridin-2-yl)aminocarbonyl]-N,N—dimethyl-1,2-benzenedisulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 21

Dust

| | |
|---|---|
| Methyl 2-[[N—(3-cyano-4,6-dimethylpyridin-2-yl)-aminocarbonyl]aminosulfonyl]benzoate | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

Test results indicate that the compounds of the present invention are active herbicides. They appear to have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. In addition, test results indicate that certain compounds are useful for selective pre- and post-emergence weed control in sugar beets. Alternatively, the subject compounds are useful for plant growth modification.

The rates of application for the compounds of the invention are determined by a number of factors, including their use as plant growth modifiers or herbicides, the species involved, the types of weeds to be controlled, weather and climate, formulations selected, mode of application, amount of foliage present, etc. In general terms, the subject compounds should be applied at levels of around 0.06 to 10 kg/ha, the lower rates being suggested for use as selective pre- and post-emergent herbicides in sugar beets, for use on lighter soils and/or those having a low organic matter content, for plant growth modification or for situations where only short-term persistence is required.

The compounds of the invention may be used in combination with any other commercial herbicide examples of which are those of the triazine, triazole, uracil, urea, amide, diphenylether, carbamate and bipyridylium types and mefluidide.

The herbicidal and plant growth modifying properties of the subject compounds were discovered in a number of greenhouse tests. The test procedures and results follow.

Test A

Seeds of crabgrass (*Digitaria* sp.), barnyardgrass (*Echinochloa crusgalli*), wild oats (*Avena fatua*), sicklepod (*Cassia obtusifolia*), morningglory (*Ipomoea* sp.), cocklebur (*Xanthium pensylvanicum*), sorghum, corn, soybean, sugar beet, rice, wheat, cotton, and purple nutsedge (*Cyperus rotundus*) tubers were planted and treated pre-emergence with the test chemicals dissolved in a non-phytotoxic solvent. At the same time, these crop and weed species, along with cotton and bush bean, were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from O=no injury, to 10=complete kill. The accompanying descriptive symbols have the following meanings:

C=chlorosis or necrosis;
D=defoliation;
E=emergence inhibition;
G=growth retardation;
H=formative effects;
U=unusual pigmentation;
X=axillary stimulation;
S=albinism; and
6Y=abscised buds or flowers.

The data indicate that at the low rates of application selected for these evaluations, most of the compounds tested are highly active herbicides. Additionally, they often possess plant growth modifying properties, such as causing growth retardation or axillary stimulation.

Compounds

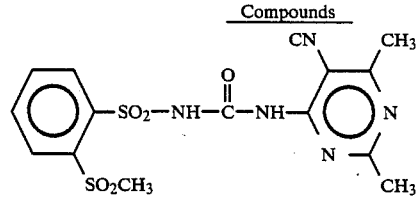
Compound 1

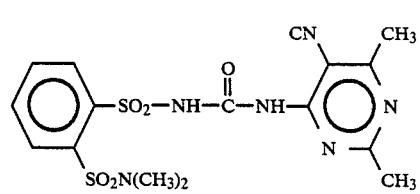
Compound 2

-continued
Compounds

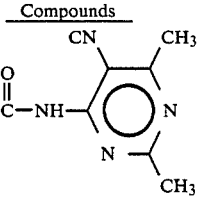
Compound 3

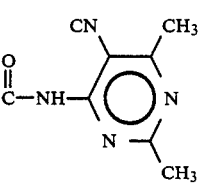
Compound 4

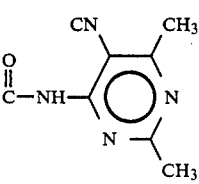
Compound 5

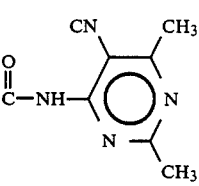
Compound 6

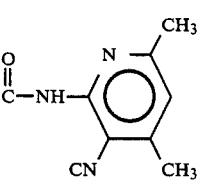
Compound 7

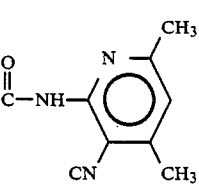
Compound 8

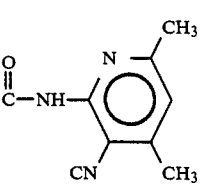
Compound 9

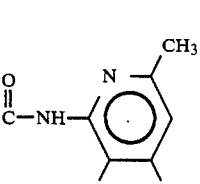
Compound 10

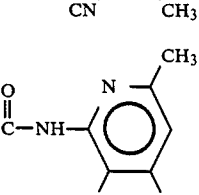
Compound 11

-continued
Compounds
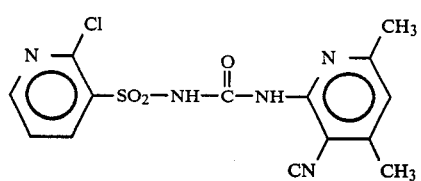 Compound 12
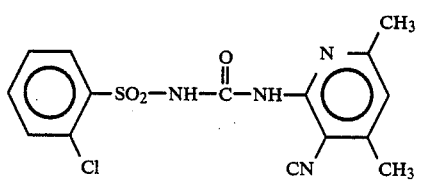 Compound 13
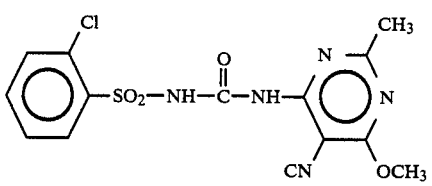 Compound 14
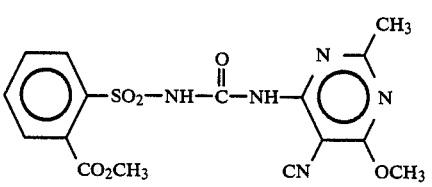 Compound 15
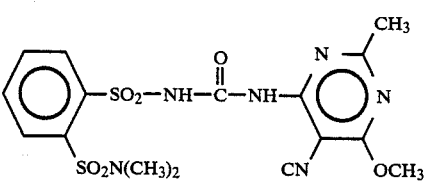 Compound 16
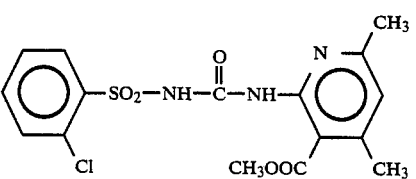 Compound 17
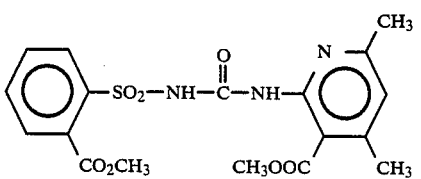 Compound 18
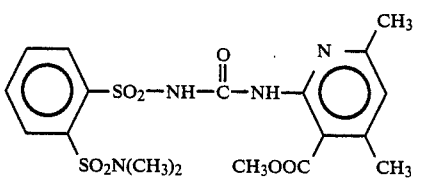 Compound 19
-continued
Compounds
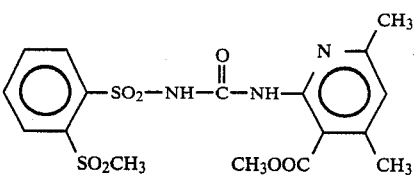 Compound 20
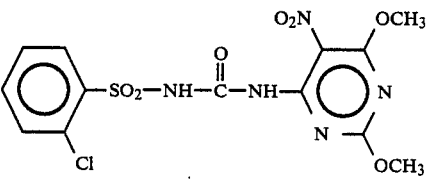 Compound 21
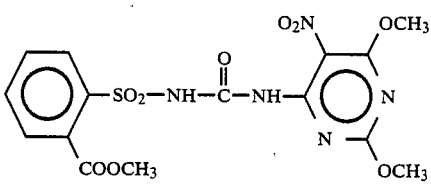 Compound 22
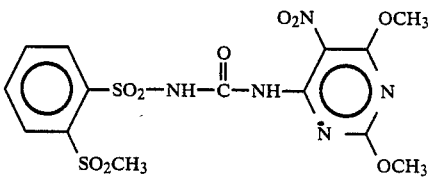 Compound 23
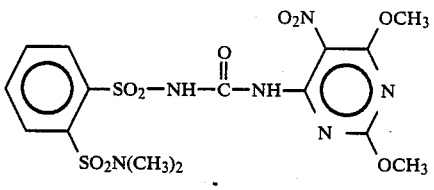 Compound 24
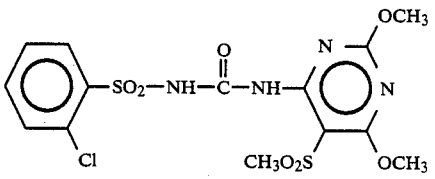 Compound 25
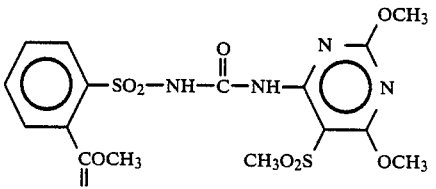 Compound 26
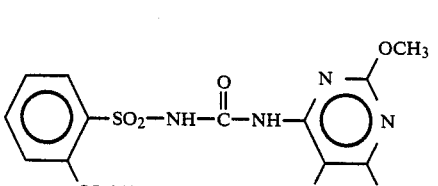 Compound 27

-continued
Compounds
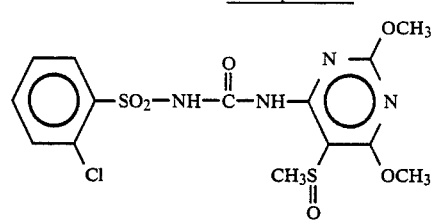 Compound 28
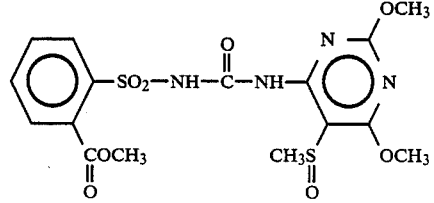 Compound 29
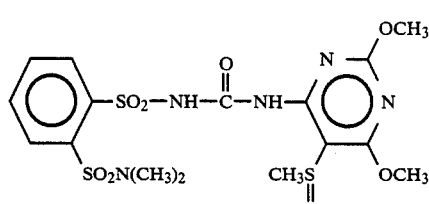 Compound 30
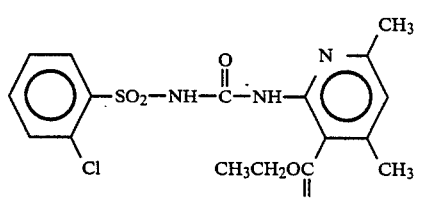 Compound 31
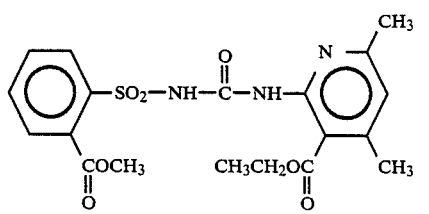 Compound 32
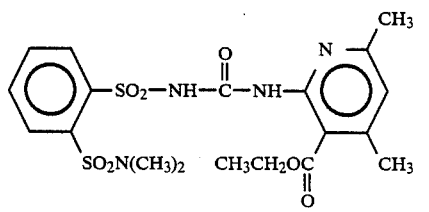 Compound 33
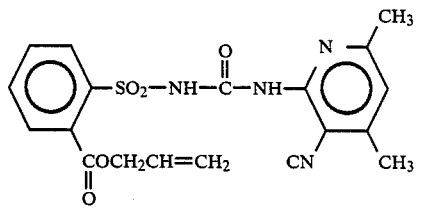 Compound 34
-continued
Compounds
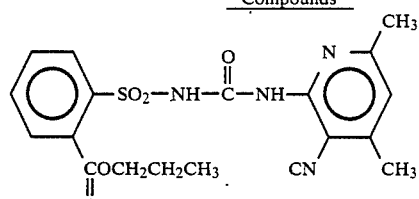 Compound 35
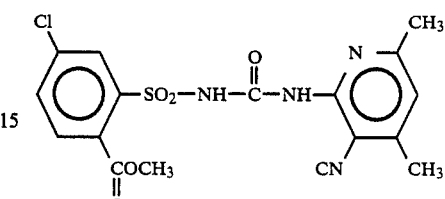 Compound 36
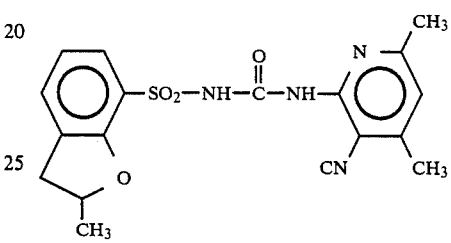 Compound 37
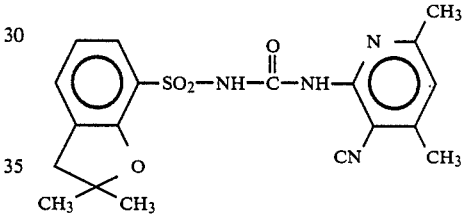 Compound 38
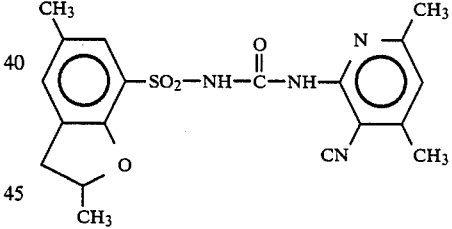 Compound 39
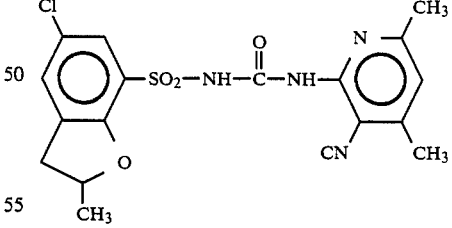 Compound 40
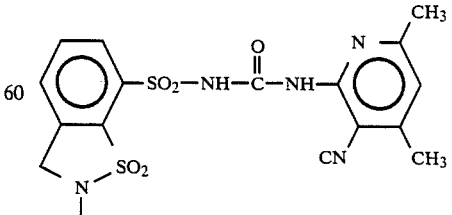 Compound 41
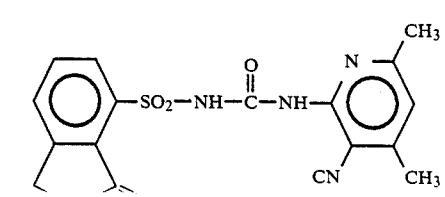 Compound 42

TABLE A

| Rate g/ha | Compound 1 | | Compound 2 | | Compound 3 | | Compound 4 | | Compound 5 | | Compound 6 | |
|---|---|---|---|---|---|---|---|---|---|---|---|---|
| | 50 | 400 | 50 | 400 | 50 | 400 | 50 | 400 | 50 | 400 | 50 | 2,000 |
| POST-EMERGENCE | | | | | | | | | | | | |
| Bush bean | 1C,1H | 4C,8G,6Y | 5C,9G,6Y | 5C,9G,6Y | 5C,9G,6Y | 6C,9G,6Y | 2C,2G,6Y | 4C,9G,6Y | 6C,9G,6Y | 6C,9G,6Y | 6Y | 5S,9D,6Y |
| Cotton | 0 | 2C,3G | 4C,9G | 5C,9G | 5C,8G | 5C,9G | 1C | 4C,8H | 5C,7H | 5C,7H | 1C,1H | 5C,9G |
| Morningglory | 2C,3G | 3C,5H | 4C,8H | 5C,9G | 4C,9G | 5C,9G | 3C,5G | 4C,8H | 4C,7H | 4C,7H | 1H | 10C |
| Cocklebur | 0 | 1C | 4C,8H | 5C,9H | 3C,7G | 5C,9G | 0 | 5C,9H | 2G | 2G | 2C,8G | 4C,9G |
| Sicklepod | 0 | 2C | 2C,3H | 5C,9H | 4C,7H | 4C,9H | 0 | 3C,5G | 1C | 1C | 2C | 5C,9G |
| Nutsedge | 0 | 2C,8G | 0 | 2C,7G | 2C,9G | 3C,8G | 0 | 3C,8G | 9G | 9G | 0 | 9G |
| Crabgrass | 1C,3G | 2C,8G | 2C,5H | 3C,9H | 2C,7H | 4C,9G | 7G | 3C,8H | 1C,5G | 1C,5G | 4G | 3C,6G |
| Barnyardgrass | 2C,6H | 4C,9H | 5C,9H | 9C | 5C,9H | 9C | 0 | 5C,9H | 2C,7H | 2C,7H | 2C,5H | 2C,9H |
| Wild Oats | 2C,6G | 4C,9H | 3C,9G | 9C | 5C,9H | 6C,9G | 2C,5G | 4C,9G | 2C,9G | 2C,9G | 2G | 2C,9G |
| Wheat | 2C,9G | 4C,9H | 3C,9G | 5U,9G | 1C,9G | 5U,9G | 2C,5H | 3C,7G | 3C,9G | 3C,9G | 0 | 2C,9G |
| Corn | 3C,9H | 5C,9G | 2U,9H | 10C | 5C,9G | 5C,9G | 3C,7H | 5C,9G | 3C,9G | 3C,9G | 4G | 9G |
| Soybean | 1C,2H | 2C,6G | 3C,9G,5X | 5C,9G | 3C,9G,5X | 5C,9G | 2C,4H | 4C,9H | 5C,9G | 5C,9G | 2U,9G | 2C,8G |
| Rice | 2C,8G | 5C,9G | 5C,9G | 6C,9G | 9C | 9C | 2C,8G | 4C,8G | 5C,9G | 5C,9G | 1C,5H | 4C,9G |
| Sorghum | 5C,9H | 5C,9G | 5C,9G | 9C | 4C,9G | 9C | 3C,5H | 2C,9G | 3C,9G | 3C,9G | 2C,5H | 9G |
| Sugar beet | 0 | 2C,5H | 4C,8G | 5C,9G | 5C,9G | 9C | 3C,6H | 4C,9G | 4C,8G | 4C,8G | 2C,6H | 2C,9G |
| PRE-EMERGENCE | | | | | | | | | | | | |
| Morningglory | 2C,2H | 2C,3H | 2C,2H | 2C,8G | 3C,6H | 5C,9G | 3C,3H | 9C | 3C,5H | 3C,5H | 2G | 9G |
| Cocklebur | 0 | 2C | 0 | 2C,8H | 0 | 4C,7H | 0 | 3C,3H | 1H | 1H | — | — |
| Sicklepod | 0 | 0 | 0 | 2C,3G | 2C | 5C,6H | 1C | 3C | 2C | 2C | 1C | 2C,4G |
| Nutsedge | 0 | 0 | 0 | 0 | 2G | 2C,7G | 0 | 2C,5G | 0 | 0 | 10E | 10E |
| Crabgrass | 0 | 0 | 2C | 2C,6G | 2C | 2C,4G | 0 | 3C,6G | 1C | 1C | 10E | 3C,8G |
| Barnyardgrass | 0 | 0 | 0 | 0 | 2C | 3C,8H | 0 | 3C,3H | 1C | 1C | 0 | 3C,9H |
| Wild Oats | 2G | 5G | 0 | 2C,6G | 4C,8G | 4C,9H | 1C,2G | 5C,9G | 3C,7G | 3C,7G | 0 | 3C,7G |
| Wheat | 2G | 8G | 4G | 3C,7G | 2C,9H | 4C,9H | 1C,2G | 4C,9G | 2C,8G | 2C,8G | 3G | 2C,9H |
| Soybean | 0 | 9C | 4G | 3C,8H | 3C,9H | 5C,9H | 2C,5G | 5C,9G | 5C,9H | 5C,9H | 2C,4G | 9G |
| Rice | 0 | 2C,6H | 1C | 3C,5H | 3C,5H | 4C,6H | 2C,3G | 4C,8H | 3C,4H | 3C,4H | 0 | 3C,5H |
| Sorghum | 0 | 2C,4G | 0 | 3C,6H | 7C,9H | 7C,9H | 2C | 5C,9H | 2C,4G | 2C,4G | 0 | 10E |
| Cotton | 3C,6G | 5C,9G | 0 | 3C,8G | 2C,2H | 5C,9G | 2C,6G | 3C,8H | 5C,9H | 5C,9H | 2C | 2C,9H |
| Sugar beet | — | 0 | — | — | — | — | — | — | — | — | — | — |

| Rate g/ha | Cmpd. 7 | | Cmpd. 8 | | Cmpd. 9 | | Cmpd. 10 | | Cmpd. 11 | | Cmpd. 12 | | Cmpd. 13 | | Cmpd. 14 | | Cmpd. 15 | | Cmpd. 16 | | Cmpd. 17 | | Cmpd. 18 | |
|---|---|---|---|---|---|---|---|---|---|---|---|---|---|---|---|---|---|---|---|---|---|---|---|---|
| | 50 | 400 | 50 | | 50 | | 50 | | 50 | | 50 | | 50 | 400 | 50 | | 50 | | 50 | | 50 | | 50 | |
| POST-EMERGENCE | | | | | | | | | | | | | | | | | | | | | | | | |
| Bush bean | 5C,9G,6Y | 9C | 4C,8G,6Y | | 2C | | 1C | | 1C,1H | | 1C | | 3C,6G,6Y | 5C,9G,6Y | 0 | | 2C,3H,6Y | | 1C | | — | | 6C,9G | |
| Cotton | 5C,9G | 6C,9G | 4C,5H | | 2C,2H | | 1C | | 4C,5H | | 2C | | 4C,6H | 5C,8H | 0 | | 2C,5G | | 1C,4G | | 2C,8G | | 6C,9G | |
| Morningglory | 4C,7G | 4C,9G | 4C,9G | | 3C,6G | | 2C | | 2C,5G | | 2C | | 2C,4G | 4C,8G | 0 | | 2C,6H | | 1C | | 2C | | 4C,8H | |
| Cocklebur | 5C,9G | 10C | 9C | | 2C | | 0 | | 4C,9G | | 1C | | 3C,9G | 5C,9G | 0 | | 2C | | 1C,5H | | 3C,9H | | 10C | |
| Sicklepod | 4C,8G | 6C,9G | 3C,5G | | 2G | | 0 | | 3C,5G | | 0 | | 2C,4H | 4C,8G | 0 | | 0 | | 0 | | 2C | | 10C | |
| Nutsedge | 9C | 10C | 3C,6G | | 2C,5G | | 2C,3H | | 5C,9G | | 0 | | 2C | 4C,9G | 0 | | 0 | | 0 | | 8G | | 9C | |
| Crabgrass | 4C,8G | 9C | 3C,9G | | 2C,8H | | 0 | | 6H | | 0 | | 3C,8H | 3C,7G | 0 | | 0 | | 3G | | 2G | | 8G | |
| Barnyardgrass | 9C | 9C | 4C,9G | | 2C,8G | | 2C,3H | | 5C,9H | | 0 | | 1C | 5C,9H | 0 | | 0 | | 2C,4G | | 1H | | 9H | |
| Wild Oats | 6C,9G | 9C | 2C,9G | | 2C | | 0 | | 2C,5G | | 2C,6H | | 1C,2G | 1C,7G | 0 | | 0 | | 0 | | 0 | | 2C,9G | |
| Wheat | 9C | 9C | 9C | | 2C,8G | | 1C | | 1C,2G | | 1C | | 1C,9G | 1C,9G | 0 | | 0 | | 1C,7G,7X | | 1C,3G | | 3C,9G | |
| Corn | 5C,9G | 10C | 5C,9G | | 2C,8G | | 2C,9G | | 2C,9G | | 2C,6H | | 2C,8G | 5U,9G | 0 | | 0 | | 2H | | 5C,9G | | 3U,9G | |
| Soybean | 5C,9G | 5C,9G | 5C,9G | | 2C,8G | | 2C,8H | | 5C,9G | | 1C | | 2C,7H | 4C,9G | 0 | | 0 | | 0 | | 9G | | 5C,9G | |
| Rice | 9C | 10C | 9C | | 2C,9G | | 2C,2H | | 3C,9H | | 1C,8G | | 3C,7H | 9C | 0 | | 0 | | 1C,2H | | 2G | | 9G | |
| Sorghum | 0 | 9C | 3C,5H | | 3C,8G | | 2C | | 5C,9G | | 2C,5H | | 4C,9G | 2C,9G | 2C,2H | | 3C,6G | | 1C,2H | | 3C,8G | | 5C,9G | |

TABLE A-continued

PRE-EMERGENCE

| | Cmpd. 19 | Cmpd. 19 | Cmpd. 20 | Cmpd. 20 | Cmpd. 21 | Cmpd. 21 | Cmpd. 22 | Cmpd. 22 | Cmpd. 23 | Cmpd. 23 | Cmpd. 24 | Cmpd. 24 | Compound 25 | Compound 25 | Compound 26 | Compound 26 | Compound 27 | Compound 27 | Compound 28 | Compound 28 | Compound 29 | Compound 29 | Compound 30 | Compound 30 |
|---|---|---|---|---|---|---|---|---|---|---|---|---|---|---|---|---|---|---|---|---|---|---|---|---|
| Rate g/ha | 50 | 400 | 50 | 400 | 50 | 400 | 50 | 400 | 50 | 400 | 50 | 400 | 50 | 400 | 50 | 400 | 50 | 400 | 50 | 400 | 50 | 400 | 50 | 400 |
| Morningglory | 2C,5G | 2C,7G | | 9C | | 9G | | 4C,9G,6Y | | 0 | | 8G | | 1C | | 2C,4G | | 3C,9H | | 1C,5H | | 2G | | 7H |
| Cocklebur | 9C | 9C | | — | | 8H | — | 9H | | 0 | | 2C,8H | | 0 | | 2C | | 2C,3H | | 2H | | 3G | | 8H |
| Sicklepod | 3C,3H | 3C,3H | | 9C | | 0 | | 8G | | 0 | | 2H | | 0 | | 2C,9G | | 2C,9H | | 2H | | 4G | | 9G |
| Nutsedge | 1C,9G | 1C,9G | | 10E | | 0 | | 9C | | 0 | | 9G | | 0 | | 10E | | 10E | | 0 | | 10E | | 10E |
| Crabgrass | 1C | 1C | | 5G | | 0 | | 0 | | 0 | | 1C | | 0 | | 2C,4G | | 2C,5H | | 2G | | 2G | | 5G |
| Barnyardgrass | 2C,7H | 2C,7H | | 5C,9H | | 4H | | 3C,5G | | 0 | | 2C,8H | | 0 | | 2C,8H | | 2C,3H | | 5G | | 1H | | 2C,8G |
| Wild Oats | 2G | 2C,9H | | 3C,9H | | 1C | | 2G | | 0 | | 3C,3H | | 0 | | 2C,8G | | 2C,7G | | 1C | | 0 | | 2C,8G |
| Wheat | 2G | 2C,9G | | 3C,9H | | 2C,8H | | 2C,9H | | 0 | | 2C,8G | | 0 | | 2C,4G | | 2C,8G | | 0 | | 0 | | 2C,8H |
| Corn | 3C,6G | 5C,9G | | 10H | | 2C,8H | | 3C,9H | | 1C | | 2C,9G | | 2C,5G | | 2C,9H | | 2C,9H | | 0 | | 0 | | 2C,9H |
| Soybean | 0 | 8H | | 9H | | 1C | | 9H | | 0 | | 3C,5H | | 1C | | 2C,7H | | 2C,5H | | 1C | | 2H | | 2C,2H |
| Rice | 9H | 10E | | 10E | | 2C,8H | | 10E | | 1C | | 10E | | 2C | | 2C,8G | | 2H | | 0 | | 6G | | 10E |
| Sorghum | 2C,7G | 7C,9H | | 6C,9H | | 2C,9H | | 3C,9H | | 5G | | 3C,8H | | 0 | | 2C,7G | | 3C,8H | | 3G | | 3G | | 3C,9H |
| Sugar beet | 1C | 4C,9G | | 5C,9G | | 8G | | 9G | | 1C | | 6C,9G | | 0 | | 5C,9G | | 6C,9G | | 2G | | 4G | | 3C,8G |
| Cotton | 0 | — | | — | | — | | — | | — | | — | | — | | — | | — | | — | | 3G | | 2C,8G |

POST-EMERGENCE

| | Cmpd. 19 | Cmpd. 19 | Cmpd. 20 | Cmpd. 20 | Cmpd. 21 | Cmpd. 21 | Cmpd. 22 | Cmpd. 22 | Cmpd. 23 | Cmpd. 23 | Cmpd. 24 | Cmpd. 24 | Compound 25 | Compound 25 | Compound 26 | Compound 26 | Compound 27 | Compound 27 | Compound 28 | Compound 28 | Compound 29 | Compound 29 | Compound 30 | Compound 30 |
|---|---|---|---|---|---|---|---|---|---|---|---|---|---|---|---|---|---|---|---|---|---|---|---|---|
| Rate g/ha | 50 | 400 | 50 | 400 | 50 | 400 | 50 | 400 | 50 | 400 | 50 | 400 | 50 | 400 | 50 | 400 | 50 | 400 | 50 | 400 | 50 | 400 | 50 | 400 |
| Bush bean | — | — | | 2C | | 2C | | 4C,9G,6Y | | 1C,3H,6Y | | 2C,7G,6Y | | 2C,4G | | 2C,4G | | 3C,9H | | 2C,5H | | 3C,5H | | 2C,9H | | 5C,9G |
| Cotton | 2C,5G | 3C,8H | | 2C | | 2C,5G | | 3C,6H | | 3C,5G | | 2C,5H | | 1C,1H | | 1C | | 5C,9G | | 2C,5H | | 3C,6G | | 3C,8H | | 5C,9G |
| Morningglory | 2C | 4C,8H | | 8G | | 5C,9G | | 9C | | 4C,9G | | 3C,8H | | 3C,4G | | 0 | | 10C | | 1C,2G | | 4C,9H | | 3C,9G | | 9C |
| Cocklebur | 2C | 4C,8H | | 2C,8G | | 3G | | 3C,5G | | 8H | | 4C,9G | | 3C,5G | | 0 | | 6C,9G | | 3C,9H | | 3C,3G | | 4C,7G | | 5C,9G |
| Sicklepod | 2G | 4C,5G | | 3G | | 0 | | 3C,5G | | 1C,2H | | 3C,5G | | 3C | | 0 | | 3G | | 2C | | 0 | | 2C,6G | | 5G |
| Nutsedge | 5G | 3G | | 3G | | 2C,8G | | 2G | | 3G | | 4G | | 0 | | 0 | | 9G | | 0 | | 0 | | 3G | | 7G |
| Crabgrass | 4G | 5G | | 0 | | 0 | | 2C,7G | | 2C,9G | | 3C,8G | | 0 | | 0 | | 4C,9G | | 2H | | 0 | | 5C,8H | | 3C,8H |
| Barnyardgrass | 5H | 2C,5H | | 2H | | 2C,8H | | 3C,8H | | 2C,5H | | 3C,9H | | 2H | | 0 | | 9C | | 3G | | 3C,7G | | 3G | | 3C,7G |
| Wild Oats | 3G | 3C,9G | | 0 | | 0 | | 2C,8H | | 2C,9H | | 2C,4G | | 0 | | 0 | | 3C,8G | | 2G | | 0 | | 5C,8H | | 5G |
| Wheat | 6G | 3C,9G | | 0 | | 2C,8H | | 2C,9G | | 2C,9G | | 4G | | 0 | | 0 | | 5G | | 3G | | 0 | | 3G | | 3C,7H |
| Corn | 2C,8H | 2C,7H | | 2G | | 0 | | 2C,8H | | 2C,8H | | 2C,8H | | 2G | | 0 | | 5C,9G | | 2C,2H | | 3C,3G | | 2C,8H | | 5C,9G |
| Soybean | 3C,9G | 4C,9G | | 1C | | 2G | | 3C,8H | | 1C,5H | | 3C,8G,5X | | 2C,2H | | 3C,3G | | 4C,9G | | 2C,5G | | 0 | | 3G | | 5C,9G |
| Rice | 9G | 5C,9G | | 6G | | 2G | | 5C,9G | | 5C,9G | | 4C,9G | | 2G | | 1C | | 6C,9G | | 2H | | 0 | | 6C,9G | | 5C,9H |
| Sorghum | 3C,8H | 4C,9G | | 1B | | 1C | | 3C,9G | | 2C,9G | | 9G | | 1C | | 0 | | 9C | | 3C,6H | | 3C,4G | | 3C,9G | | 3C,9H |
| Sugar beet | 2C,2G | 3C,8H | | 4B | | 4B | | 3C,8H | | 3G | | 4C,8H | | 2C,6H | | 3C,7G | | | | 3C,6H | | 3C,6G | | 5C,9G | | 5C,9G |
| Cotton | — | — | | — | | — | | — | | — | | — | | — | | — | | — | | — | | — | | — | | 8G |

PRE-EMERGENCE

| | Cmpd. 19 | Cmpd. 19 | Cmpd. 20 | Cmpd. 20 | Cmpd. 21 | Cmpd. 21 | Cmpd. 22 | Cmpd. 22 | Cmpd. 23 | Cmpd. 23 | Cmpd. 24 | Cmpd. 24 | Compound 25 | Compound 25 | Compound 26 | Compound 26 | Compound 27 | Compound 27 | Compound 28 | Compound 28 | Compound 29 | Compound 29 | Compound 30 | Compound 30 |
|---|---|---|---|---|---|---|---|---|---|---|---|---|---|---|---|---|---|---|---|---|---|---|---|---|
| Morningglory | 9G | 2C,8H | | 3C,9G | | 5C,9G | | 9H | | 2C,6H | | 3C,9G | | 1C | | 2C,1H | | 2C,3H | | 3C,5H | | 9G | | 3C,7H | | 8G |
| Cocklebur | 2C,5G | — | | 9H | | 9H | | 9H | | 6H | | 9H | | 0 | | 2C,2H | | 2C,3H | | 1H | | 4C,7G | | 9H | | 9H |
| Sicklepod | 2C | 2C | | 8G | | 9G | | 9G | | 2C,4G | | 7G | | 0 | | 0 | | 2C,5H | | 0 | | 2C,5G | | 4C,5G | | 3C,7G |
| Nutsedge | 0 | 2C | | 2C,8G | | 4G | | 4G | | 0 | | 5G | | 0 | | 0 | | 0 | | 0 | | 0 | | 1C | | 0 |
| Crabgrass | 2G | 2G | | 0 | | 0 | | 2G | | 2C,5G | | 1C | | 2G | | 0 | | 2C | | 0 | | 0 | | 2C,3H | | 3C,6G |
| Barnyardgrass | 1H | 2C,2H | | 1C | | 2C,9H | | 2C,9H | | 5H | | 2C,8H | | 0 | | 0 | | 3C,9H | | 2G | | 3C,9H | | 1C | | 3C,6G |
| Wild Oats | 2G | 2C,5G | | 0 | | 3C,9H | | 3C,9H | | 2C,9G | | 2C,7G | | 0 | | 0 | | 3C,8G | | 3G | | 3C,8G | | 1C | | 6G |
| Wheat | 2G | 7G | | 0 | | 9H | | 9H | | 9H | | 8G | | 0 | | 0 | | 2C,7G | | 2G | | 2C | | 1C | | 3C,8G |
| Corn | 3C,6G | 2C,8G | | 6G | | 1C | | 2C,9H | | 2C,9H | | 2C,5H | | 2G | | 5G | | 5G | | 2C,3G | | 2C,5G | | 2C,5H | | 3C,6H |
| Soybean | 0 | 2H | | 1C | | 2H | | 3C,7H | | 1C,1H | | 2C,3H | | 0 | | 2C | | 2C | | 1H | | 2C | | 2C,8H | | 4C,7G |
| Rice | 9H | 9H | | 3C,8H | | 10E | | 10E | | 10E | | 10E | | 0 | | 0 | | 10E | | 5G | | 2C | | 10E | | 3C,9H |
| Sorghum | 2C,7G | 3C,9G | | 0 | | 3C,8H | | 5C,9H | | 3C,9H | | 5C,9G | | 2G | | 2C,3G | | 5C,9H | | 2C,7H | | 2C,4G | | 2C,9G | | 5C,9G |
| Sugar beet | 1C | 2C | | 9G | | 8G | | 9G | | 8G | | 5C,9G | | 5H | | 3C,7G | | 5C,9G | | 2C,7H | | 2C,6H | | 3C,8G | | 5C,9G |
| Cotton | 0 | 2G | | — | | — | | — | | — | | — | | 0 | | 2C,7G | | 2G | | 0 | | 2G | | 3C,7G | | 8G |

TABLE A-continued

| Rate g/ha | Compound 30 50 | Cmpd. 31 50 | Cmpd. 32 50 | Cmpd. 33 50 | Cmpd. 34 50 | Cmpd. 35 50 | Cmpd. 36 50 | Cmpd. 37 50 | Cmpd. 38 50 | Cmpd. 39 50 | Cmpd. 40 50 | Cmpd. 41 50 | Cmpd. 42 50 |
|---|---|---|---|---|---|---|---|---|---|---|---|---|---|
| POST-EMERGENCE |
| Morningglory | 3C,6G | 1C | 2C,4G | 1C,2H | 2G | 2G | 2C,3G | 1C | 2G | 3G | 1C,3G | 3C,6H | 2C,5G |
| Cocklebur | 4C,9G | 2C,8H | 4C,9G | 3C,9H | 2C,8H | 3C,8H | 3C,9G | 9C | 1C | 2C,8G | 3C,8G | 2C,6H | 3C,8G |
| Sicklepod | 4C,8H | 2C | 5C,9G | 3C,8H | 0 | 0 | 2C | 3C,7G | 0 | 3G | 0 | 3G | 3C,5G |
| Nutsedge | 2G | 3C,9G | 2C,9G | 2C,8G | 0 | 5G | 3C,8G | 3C,7G | 0 | 0 | 0 | 0 | 3G |
| Crabgrass | 3G | 0 | 0 | 3G | 0 | 1C | 4G | 6G | 0 | 0 | 0 | 0 | 2G |
| Barnyardgrass | 4H | 0 | 2G | 2C,4H | 2C,7H | 2C,5H | 3C,9H | 9C | 6H | 0 | 0 | 5H | 3C,6H |
| Wild Oats | 0 | 0 | 2C,9H | 0 | 2C,5G | 0 | 3C,8G | 9C | 0 | 0 | 0 | 0 | 2C,5G |
| Wheat | 6G | 0 | 9C | 7G | 2C,5G | 2C,8H | 2C,8G | 6C,9G | 1H | 0 | 0 | 2G | 2C,8G |
| Corn | 2C,4H | 0 | 5C,9G | 3C,8H | 3C,9H | 1C,1H | 1C,7G | 3C,9G | 3H | 1C,2G | 3H | 2C,7H | 2C,6H |
| Soybean | 3C,9G,7X | 1H | 4C,9G | 3C,8H | 1C | 2C,8G | 1C,9G | 5C,9G | 3H | 6G | 6G | 2C,2H | 2C,6H |
| Rice | 2C,9G | 6G | 5C,9G | 9G | 9G | 2C,8H | 5C,9G | 5C,9G | 4G | 3C,8H | 2C,8H | 2C,8G | 2C,2H |
| Sorghum | 3C,7H | 0 | 2C,9H | 3C,9H | 2C,9G | 2C,8H | 3C,9H | 5C,9G | 2C,6G | 2C,5G | 1C,3H | 2H | 2C,5G |
| Sugar beet | 3C,8H | 9C | 9C | 2C,3G | 3C,6H | 3C,6G | 2C,4G | 5C,8G | 1H | 6G | 3G | 2C,6H | 1C |
| Cotton | 2C,9H | 7G,2C | 9C | 5C,9G | 2G | 3C,8H | 2C,8G | 2C,9G | 2G | | | 2G | 2C,7G |
| | | | | | | | | | | | | | 2G |
| PRE-EMERGENCE |
| Morningglory | 2C,6G | 2H | 2G | 2G | 0 | 0 | 2G | 3C,6G | 0 | 2C,3H | 0 | 7H | 0 |
| Cocklebur | 3C,7H | 2H | 2C,7H | 2C,5H | 0 | 0 | 8H | 9H | 2H | 9H | 9H | 2G | 0 |
| Sicklepod | 2C,5G | 2G | 2C | 0 | 0 | 0 | 2G | 5G | 1C | 1C | 0 | 0 | 0 |
| Nutsedge | 0 | 5C,9G | 10E | 2C,5G | 0 | 0 | 3G | 2G | 0 | 0 | 0 | 0 | 0 |
| Crabgrass | 0 | 2C | 1C | 2G | 0 | 0 | 0 | 0 | 0 | 0 | 0 | 2H | 0 |
| Barnyardgrass | 0 | 1C | 2C,8G | 2C | 0 | 0 | 4H | 5G | 0 | 0 | 0 | 0 | 0 |
| Wild Oats | 1C | 0 | 2C,8G | 4G | 0 | 0 | 2G | 3C,9G | 1H | 0 | 0 | 0 | 0 |
| Wheat | 0 | 0 | 2C,9H | 3C,8H | 3G | 2G | 0 | 2C,5G | 0 | 2C,7G | 0 | 0 | 0 |
| Corn | 2C,6G | 5G | 2C | — | 0 | 0 | 2C,5G | 2C,9H | 0 | 0 | 1C | 2G | 0 |
| Soybean | 2C,4G | 0 | 3C,8H | 3C,5G | 2G | 0 | 2C,2H | 1C,1H | 1H | 0 | 0 | 1H | 0 |
| Rice | 2C,5G | 0 | 2C,9G | 3C,6G | 0 | 0 | 3C,8H | 5C,9H | 0 | 0 | 2C | 5G | 0 |
| Sorghum | 3C,7G | 5C,9G | 2C,9G | 8G | 2G | 7H | 3C,6G | 5C,9H | 0 | 6G | 2C | 0 | 0 |
| Sugar beet | 2C,8G | 6G | 5C,9G | 5G | 7H | 0 | 7G | 9H | 2G | 3G | 2H | 0 | 0 |
| Cotton | 2C,6G | | 8G | | 1C | | 5G | 9G | | | 2G | | |

The following test was performed to better define the pre-emergence activity of the claimed compounds.

Test B

Two plastic bulb pans were filled with fertilized and limed Woodstown sandy loam soil. One pan was planted with corn, sorghum, Kentucky bluegrass and several grass weeds. The other pan was planted with cotton, soybeans, purple nutsedge (*Cyperus rotundus*), and several broadleaf weeds. The following grass and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with several test compounds within the scope of the invention.

Twenty-eight days after treatment, the plants were evaluated and visually rated for response to the chemical treatments utilizing the rating system described previously for Test A. Results for several of the more active compounds are presented in Table B. Almost all of the compounds tested showed pre-emergence activity on a number of species at rates as low as 31 g/ha; some were active at even lower rates. At higher rates, e.g. 125 g/ha, most compounds exhibited broad spectrum pre-emergence activity.

TABLE B

PRE-EMERGENCE ON WOODSTOWN SANDY LOAM

| Rate g/ha | Compound 7 | | Compound 8 | |
|---|---|---|---|---|
| | 8 | 62 | 31 | 250 |
| Crabgrass | 0 | 0 | 0 | 7G |
| Barnyardgrass | 0 | 7G | 0 | 5G |
| Sorghum | 6G | 9G | 8G | 9G |
| Wild Oats | 0 | 2G | 0 | 0 |
| Johnsongrass | 5G | 9G | 4G | 8G |
| Dallisgrass | 0 | 4G | 0 | 5G |
| Giant foxtail | 0 | 0 | 0 | 7G |
| Ky. bluegrass | 0 | 5G | 2G | 9G |
| Cheatgrass | 0 | 9G | 0 | 7G |
| Sugar beets | 5G | 9G | 5G | 7G |
| Corn | 7G | 8G | 3G | 7G |
| Mustard | 9G | 9G | 8G | 9G |
| Cocklebur | 0 | 8G | — | 8G |
| Nutsedge | 0 | 9G | 0 | 6G |
| Cotton | 3G | 3G | 3G | 5G |
| Morningglory | 0 | 2G | 0 | 0 |
| Sicklepod | 0 | 3G | 2G | 3G |
| Teaweed | 3G | 6G | 0 | 0 |
| Velvetleaf | 0 | 2G | 0 | 2G |
| Jimsonweed | 2G | 4G | 0 | 0 |
| Soybean | 0 | 7G,7H | 0 | 2G |
| Rice | 6G | 10C | 5G | 10C |
| Wheat | 0 | 6G | 0 | 8G |

| Rate g/ha | Compound 22 | |
|---|---|---|
| | 31 | 125 |
| Crabgrass | 0 | 3G |
| Barnyardgrass | 0 | 3G |
| Sorghum | 9G | 10C |
| Wild Oats | 0 | 3G |
| Johnsongrass | 4G | 5G |
| Dallisgrass | 0 | 7G |
| Giant foxtail | 3G | 8G |
| Ky. bluegrass | 6G | 10C |
| Cheatgrass | 7G | 10C |
| Sugar beets | 6G | 8G |
| Corn | 3G | 9G |
| Mustard | 8G | 9G |
| Cocklebur | 7G | 7G |
| Nutsedge | 2G | 4G |
| Cotton | 2G | 8G |
| Morningglory | 2G | 2G |
| Sicklepod | 0 | 2G |
| Teaweed | 0 | 0 |
| Velvetleaf | 2G | 4G |
| Jimsonweed | 2G | 7G |
| Soybean | 0 | 3G |
| Rice | 10C | 10C |
| Wheat | 0 | 2G |

The following test was performed to better define the post-emergence activity of the claimed compounds.

Test C

The test chemicals, dissolved in a non-phytotoxic solvent, were applied in an overall spray to the foliage and surrounding soil of selected plant species. One day after treatment, plants were observed for rapid burn injury. Approximately fourteen days after treatment, all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), sicklepod (*Cassia obtusifolia*), morningglory (*Ipomoea hederacea*), jimsonweed (*Datura stramonium*), cocklebur (*Xanthium pensylvanicum*), crabgrass (*Digitaria* sp.), nutsedge (*Cyperus rotundus*), barnyardgrass (*Echinochloa crusgalli*), giant foxtail (*Setaria faberii*) and wild oats (*Avena fatua*). The following species were grown in soil in a paper cup (12 cm diameter by 13 cm deep): sunflower, sugar beets, and mustard. All plants were sprayed approximately 14 days after planting. Additional plant species are sometimes added to this standard test in order to evaluate unusual selectivity.

Results for two of the most active compounds tested in this screen are presented in Table C. Many of the other compounds also showed post-emergence activity at rates as low as 4 or 16 g/ha.

TABLE C

Over-the-Top Soil/Foliage Treatment

| Rate g/ha | Compound 7 | | |
|---|---|---|---|
| | 4 | 16 | 61 |
| Soybeans | 10C | 10C | 10C |
| Velvetleaf | 7G,7C | 9C | 10C |
| Sesbania | 7G | 9G | 9G |
| Sicklepod | 7G | 9G | 9G |
| Cotton | 9G | 10C | 10C |
| Morningglory | 7G,5C | 8G | 8G |
| Alfalfa | 7G,6C | 7C,8G | 8C,9G |
| Jimsonweed | 4G | 6G | 9G |
| Cocklebur | 8G | 9G | 9G |
| Sunflower | 8C,7G | 10C | 10C |
| Mustard | 6G | 8G | 10C |
| Sugar beets | 8G | 10C | 10C |
| Corn | 10C | 10C | 10C |
| Crabgrass | 6G | 3G | 6G |
| Rice | 9C | 8C,8G | 9C |
| Nutsedge | 7G | 7G | 7G |
| Barnyardgrass | 10C | 10C | 10C |

TABLE B-continued

| Cheatgrass | 7G | 10C |
| Sugar beets | 6G | 8G |
| Corn | 3G | 9G |
| Mustard | 8G | 9G |
| Cocklebur | 7G | 7G |
| Nutsedge | 2G | 4G |
| Cotton | 2G | 8G |
| Morningglory | 2G | 2G |
| Sicklepod | 0 | 2G |
| Teaweed | 0 | 0 |
| Velvetleaf | 2G | 4G |
| Jimsonweed | 2G | 7G |
| Soybean | 0 | 3G |
| Rice | 10C | 10C |
| Wheat | 0 | 2G |

TABLE C-continued

| | | Compound 7 | |
|---|---|---|---|
| Wheat | 6C,7G | 6G | 6C,7G |
| Giant foxtail | 9G | 6G | 9G |
| Wild Oats | 8G | 8G | 8G |
| Sorghum | 9G | 9G | 9G |
| Johnsongrass | 9G | 9G,9C | 9G |
| Field Bindweed | 7G | 5G | 7G |

| | Compound 8 | | |
|---|---|---|---|
| Rate g/ha | 4 | 16 | 61 |
| Soybeans | 8G,9C | 10C | 10C |
| Velvetleaf | 6G | 9G,7C | 10C |
| Sesbania | 8G | 9G | 9G |
| Sicklepod | 4G | 8G | 9G |
| Cotton | 9G | 9G | 10C |
| Morningglory | 7G | 7G,6C | 8G,7C |
| Alfalfa | 2G,1C | 7G,6C | 10C |
| Jimsonweed | 0 | 4G | 6G |
| Cocklebur | 8G | 9G | 10C |
| Sunflower | 8G | 10C | 10C |
| Mustard | 7G | 8G | 9G |
| Sugar beets | 7G | 8G | 10C |
| Corn | 6G | 7G | 7G |
| Crabgrass | 4G | 7G | 9G |
| Rice | 6G | 9C | 10C |
| Nutsedge | 0 | 2G | 4G |
| Barnyardgrass | 7G | 9C,7G | 10C |
| Wheat | 6G | 7G | 8G |
| Giant foxtail | 3G | 6G | 8G |
| Wild Oats | 5G | 7G | 8G |
| Sorghum | 8G | 9G | 9G |
| Johnsongrass | 8G | 9C | 9C |
| Field Bindweed | 0 | 2G | 4G |

Test D

Two 25-cm in diameter plastic pans lined with polyethylene liners were filled with prepared Sassafras loamy sand soil. One pan was planted with seeds of wheat (*Triticum aestivum*), barley (*Hordeum vulgare*), wild oats (*Avena fatua*), blackgrass (*Alopecurus myosuroides*), annual bluegrass (*Poa annua*), green foxtail (*Setaria viridis*) and Italian ryegrass (*Lolium multiflorum*). The other pan was planted with seeds of wild radish (*Raphanus naphanistrum*), kochia (*Kochia scoparia*), *Matricaria inodora*, black nightshade (*Solanum nigrum*), wild mustard (*Brassica kaber*), wild buckwheat (*Polygonum convolvulus*), Galium aparine, Veronica persica and sugar beets (*Beta vulgaris*). The above two pans were treated pre-emergence. At the same time two pans in which the above plant species were growing were treated post-emergence. Plant height at the time of treatment ranged from 1–15 cm depending on plant species.

The test compound was diluted with a non-phytotoxic solvent and sprayed over-the-top of the pans. An untreated control and a solvent-alone control were included for comparison. All treatments were maintained in the greenhouse for 21 days at which time the treatments were compared to the controls and the effects visually rated utilizing the rating system as described in Test A. The recorded data are presented in Table D. The data indicate that the compound tested has utility for selective weed control in sugar beets.

TABLE D

| Pre-Emergence | Compound 19 | | | | |
|---|---|---|---|---|---|
| Rate g/ha | 4 | 16 | 64 | 125 | 250 |
| wheat | 0 | 0 | 0 | — | — |
| barley | 0 | 0 | 0 | — | — |
| wild oats | 0 | 0 | 0 | — | — |
| ryegrass | 0 | 0 | 4G | — | — |
| annual bluegrass | 0 | 1G | 4G | — | — |
| blackgrass | 0 | 3G | 2G | — | — |
| green foxtail | 0 | 0 | 0 | — | — |
| *Matricaria inodora* | 1G | 5G | 6G | — | — |
| *Galium aparine* | 4G,3C | 4G,3C | 7G | — | — |
| kochia | 0 | 0 | 0 | 0 | 0 |
| black nightshade | 5G,4C | 4G,7C | 8G,9C | 8G,7C | 9G |
| speedwell | 3G | 10C | 10C | — | — |
| wild buckwheat | 0 | 5G,3C | 7G | 8G,8C | 10C |
| wild mustard | 0 | 5G,4C | 9G,9C | 9G | 10C |
| wild radish | 3G | 9G | 9G | — | — |
| sugar beets | 0 | 0 | 0 | 1G | 1G |
| Post-Emergence | | | | | |
| Rate g/ha | 4 | 16 | 64 | 125 | 250 |
| wheat | 0 | 0 | 3G | — | — |
| barley | 0 | 0 | 3G | — | — |
| wild oats | 0 | 0 | 2G | — | — |
| ryegrass | 0 | 0 | 1G | — | — |
| annual bluegrass | 0 | 0 | 0 | — | — |
| blackgrass | 0 | 0 | 0 | — | — |
| green foxtail | 0 | 0 | 0 | — | — |
| *Matricaria inodora* | 1C | 1G,3C | 4G,3C | — | — |
| *Galium aparine* | 2G | 9G | — | — | — |
| kochia | — | 0 | 3G | 0 | 0 |
| black nightshade | 1G,1C | 3C | 3C | 5G,3C | 9G,8C |
| speedwell | 7G,5C | 7G,4C | 8G | — | — |
| wild buckwheat | 9G,7C | 9G,8C | 9G | 4G | 10C |
| wild mustard | 9G,8C | 9G,7C | 10C | 3G | 10C |
| wild radish | 10C | 10C | 10C | — | — |
| sugar beets | 0 | 0 | 3G | 4G,3C | 8G,8C |

What is claimed is:

1. A compound of the formula:

$$JSO_2NHC(=W_1)N(R)-A \quad \text{I}$$

wherein

J is

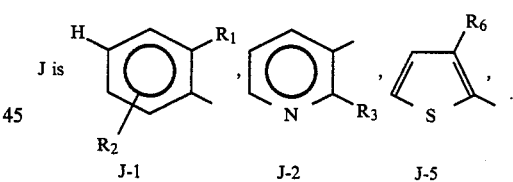

J-1, J-2, J-5

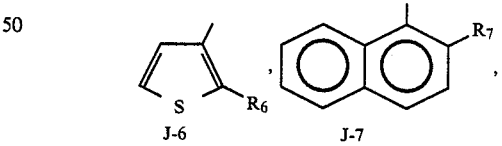

J-6, J-7

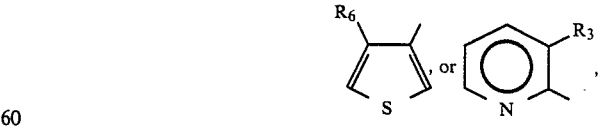

J-14, or J-15

$W_1$ is O or S;

R is H or $CH_3$;

$R_1$ is $NO_2$, F, Cl, Br, $CF_3$, $C_1$–$C_3$ alkyl, $C_1$–$C_2$ alkyl substituted with $OCH_3$ or $OC_2H_5$, $SO_2N(CH_3)R_{10}$, $S(O)_nR_{11}$, $S(O)_nCF_2H$, $S(O)_nCF_3$, $OR_{12}$, $OSO_2R_{11}$, $CH_2CH_2Cl$, $C(O)R_{25}$,

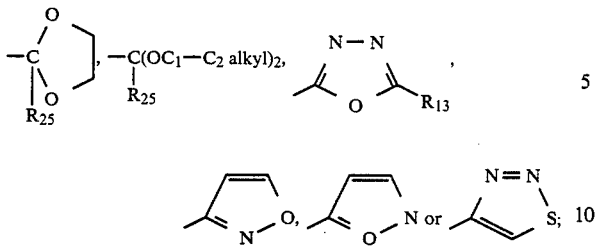

R$_2$ is H, C$_1$-C$_2$ alkyl, C$_1$-C$_2$ alkoxy, C$_1$-C$_2$ alkylthio, C$_1$-C$_2$ alkylsulfinyl, C$_1$-C$_2$ alkylsulfonyl, C$_1$-C$_2$ haloalkyl or halogen;

R$_3$ is Cl, SO$_2$CH$_3$, SO$_2$N(CH$_3$)$_2$, OCH$_3$, NO$_2$ or N(CH$_3$)$_2$;

R$_6$ is CO$_2$R$_9$, S(O)$_n$R$_{11}$, C$_1$-C$_3$ alkyl, Cl, Br or SO$_2$N(CH$_3$)$_2$;

R$_7$ is S(O)$_n$R$_{11}$, OSO$_2$R$_{11}$, C$_1$-C$_3$ alkyl, C$_1$-C$_3$ alkoxy or Cl;

R$_9$ is C$_1$-C$_3$ alkyl, CH$_2$CH=CH$_2$, CH$_2$CH$_2$Cl or CH$_2$CH$_2$OCH$_3$;

R$_{10}$ is C$_1$-C$_3$ alkyl or OCH$_3$;

R$_{11}$ is C$_1$-C$_3$ alkyl;

R$_{12}$ is C$_1$-C$_3$ alkyl, CH$_2$CH$_2$OCH$_3$, C$_3$-C$_4$ alkenyl, C$_3$-C$_4$ alkynyl or C$_1$-C$_3$ alkyl substituted with 1-3 atoms of Cl or F, or with 1 Br;

R$_{13}$ is H or CH$_3$; n is 0, 1 or 2;

A is

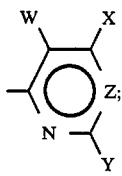 A-1

W is CN;

X is CH$_3$, OCH$_3$, OC$_2$H$_5$, CH$_2$OCH$_3$, Cl, CH$_2$OH, NHCH$_3$ or N(CH$_3$)$_2$;

Y is CH$_3$, OCH$_3$, OC$_2$H$_5$ or Cl;

Z is CH;

R$_{25}$ is H or C$_1$-C$_2$ alkyl;

and their agriculturally suitable salts; provided that X and Y cannot simultaneously be Cl.

2. A compound of claim 1 wherein
W$_1$ is O;
J is

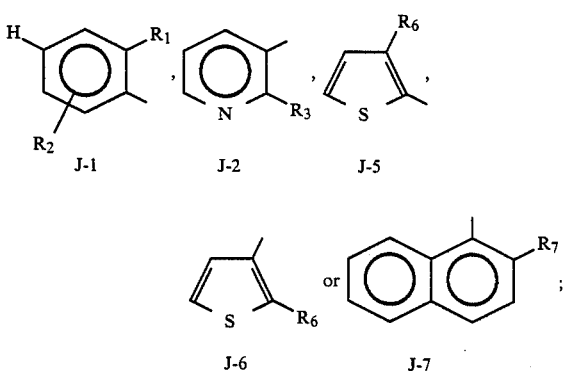

R$_1$ is NO$_2$, F, Cl, Br, CF$_3$, C$_1$-C$_3$ alkyl, CH$_2$CH$_2$OCH$_3$, CH$_2$OCH$_3$, SO$_2$N(CH$_3$)R$_{10}$, S(O)$_n$R$_{11}$, SCF$_2$H, OR$_{12}$, OSO$_2$R$_{11}$, R$_2$ is H, F, Cl, Br, CH$_3$, OCH$_3$ or CF$_3$;

R$_3$ is Cl, SO$_2$CH$_3$ or SO$_2$N(CH$_3$)$_2$; R$_6$ is C$_1$-C$_3$ alkyl, CO$_2$R$_{11}$, S(O)$_n$R$_{11}$, Cl or Br;

R$_7$ is S(O)$_n$R$_{11}$, OSO$_2$R$_{11}$, C$_1$-C$_3$ alkyl, C$_1$-C$_3$ alkoxy or Cl;

R$_9$ is C$_1$-C$_3$ alkyl, CH$_2$CH=CH$_2$, CH$_2$CH$_2$Cl or CH$_2$CH$_2$OCH$_3$;

R$_{10}$ is C$_1$-C$_3$ alkyl or OCH$_3$;

R$_{11}$ is C$_1$-C$_3$ alkyl;

R$_{12}$ is C$_1$-C$_3$ alkyl, CF$_2$H or CH$_2$CH$_2$OCH$_3$;

R$_{13}$ is H or CH$_3$;

n is 0 or 2;

R is H or CH$_3$;

A is

W is CN;
X is CH$_3$, OCH$_3$, OC$_2$H$_5$, CH$_2$OCH$_3$ or Cl;
Y is CH$_3$, OCH$_3$, OC$_2$H$_5$ or Cl; and
Z is CH;
provided that X and Y cannot simultaneously be Cl;

3. A compound of claim 1 where R is H and W$_1$ is oxygen.

4. A compound of claim 3 where J is J-1.

5. A compound of claim 4 where R$_1$ is F, Cl, Br, NO$_2$, CH$_3$, OCH$_3$, OC$_2$H$_5$, OCH$_2$CH=CH$_2$, CF$_3$, CH$_2$CH$_2$OCH$_3$, SO$_2$N(CH$_3$)$_2$, SO$_2$CH$_3$, SO$_2$C$_2$H$_5$, OSO$_2$CH$_3$ or OSO$_2$C$_2$H$_5$; and R$_2$ is H, F, Cl, CH$_3$, OCH$_3$ or SCH$_3$.

6. A compound of claim 5 where X and Y are independently CH$_3$.

7. A compound of claim 3 where J is J-5.

8. A compound of claim 7 where X and Y are independently CH$_3$ or OCH$_3$.

9. The compound of claim 1 which is N'-N,N-dimethyl-1,2-benzenedisulfonamide.

10. A herbicidal composition comprising an herbicidally effective amount of a compound of claim 1 and at least one of (a) a surfactant and (b) a solid or liquid diluent.

11. A herbicidal composition comprising an herbicidally effective amount of a compound of claim 2 and at least one of (a) a surfactant and (b) a solid or liquid diluent.

12. A herbicidal composition comprising an herbicidally effective amount of a compound of claim 3 and at least one of (a) a surfactant and (b) a solid or liquid diluent.

13. A herbicidal composition comprising an herbicidally effective amount of a compound of claim 4 and at least one of (a) a surfactant and (b) a solid or liquid diluent.

14. A herbicidal composition comprising an herbicidally effective amount of a compound of claim 5 and at least one of (a) a surfactant and (b) a solid or liquid diluent.

15. A herbicidal composition comprising an herbicidally effective amount of a compound of claim 6 and at least one of (a) a surfactant and (b) a solid or liquid diluent.

16. A herbicidal composition comprising an herbicidally effective amount of a compound of claim 7 and at least one of (a) a surfactant and (b) a solid or liquid diluent.

17. A herbicidal composition comprising an herbicidally effective amount of a compound of claim 8 and at least one of (a) a surfactant and (b) a solid or liquid diluent.

18. A herbicidal composition comprising an herbicidally effective amount of a compound of claim 9 and at least one of (a) a surfactant and (b) a solid or liquid diluent.

19. A method of controlling the growth of undesired vegetation comprising applying to the locus of such vegetation an herbicidally effective amount of a compound of claim 1.

20. A method of controlling the growth of undesired vegetation comprising applying to the locus of such vegetation an herbicidally effective amount of a compound of claim 2.

21. A method of controlling the growth of undesired vegetation comprising applying to the locus of such vegetation an herbicidally effective amount of a compound of claim 3.

22. A method of controlling the growth of undesired vegetation comprising applying to the locus of such vegetation an herbicidally effective amount of a compound of claim 4.

23. A method of controlling the growth of undesired vegetation comprising applying to the locus of such vegetation an herbicidally effective amount of a compound of claim 5.

24. A method of controlling the growth of undesired vegetation comprising applying to the locus of such vegetation an herbicidally effective amount of a compound of claim 6.

25. A method of controlling the growth of undesired vegetation comprising applying to the locus of such vegetation an herbicidally effective amount of a compound of claim 7.

26. A method of controlling the growth of undesired vegetation comprising applying to the locus of such vegetation an herbicidally effective amount of a compound of claim 8.

27. A method of controlling the growth of undesired vegetation comprising applying to the locus of such vegetation an herbicidally effective amount of a compound of claim 9.

* * * * *

UNITED STATES PATENT AND TRADEMARK OFFICE
CERTIFICATE OF CORRECTION

PATENT NO. : 4,906,288
DATED : March 6, 1990
INVENTOR(S) : Caleb W. Holyoke, Jr., Chi-Ping Tseng and William T. Zimmerman It is certified that error appears in the above-identified patent and that said Letters Patent is hereby corrected as shown below:

Column 4, lines 40-45 structural formaul A-Z add a single bond as are present for A-1, A-3 and A-4.

Column 12, line 42 delete " (C=) " and add therefore -- (C≡N) --.

Column 31, under Table III-f delete the structural formula and add the structure shown below:

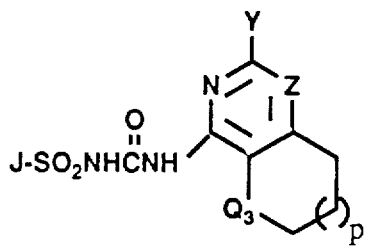

Column 33, under Table III-f delete the structural formula and add the structure shown below:

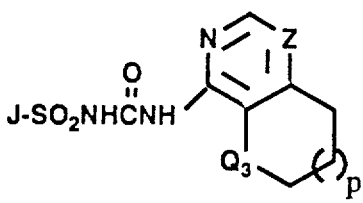

UNITED STATES PATENT AND TRADEMARK OFFICE
CERTIFICATE OF CORRECTION

PATENT NO. : 4,906,288

DATED : March 6, 1990

INVENTOR(S) : Caleb W. Holyoke, Jr., Chi-Ping Tseng and William T. Zimmerman

It is certified that error appears in the above-identified patent and that said Letters Patent is hereby corrected as shown below:

Page 2 of 2

Claim 1, column 55, line 10 delete the structure " 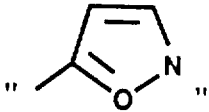 "

and add the structure -- 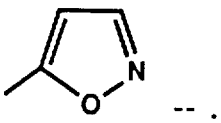 -- .

Claim 2, column 56, line 13 before the definition of " $R_7$ " add -- $R_6$ is $C_1$-$C_3$ alkyl, $CO_2R_{11}$, $S(O)_nR_{11}$, Cl or Br; -- .

Col. 56 Ln 52,53 delete " N'-N,N-dimethyl-1,2-benzenedisulfonamide" and add -- N'-[(3-cyano-4,6-dimethylpyridin-2-yl)aminocarbonyl]-N,N-dimethyl-1,2-benzenedisulfonamide" -- .

Signed and Sealed this

Thirtieth Day of July, 1991

Attest:

HARRY F. MANBECK, JR.

Attesting Officer

Commissioner of Patents and Trademarks